(12) United States Patent
Hummer

(10) Patent No.: US 11,832,152 B2
(45) Date of Patent: *Nov. 28, 2023

(54) METHOD AND DEVICES FOR DETECTING VIRUSES AND BACTERIAL PATHOGENS

(71) Applicant: Gregory J. Hummer, Shaker Heights, OH (US)

(72) Inventor: Gregory J. Hummer, Shaker Heights, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/498,601

(22) Filed: Oct. 11, 2021

(65) Prior Publication Data

US 2022/0124465 A1 Apr. 21, 2022

Related U.S. Application Data

(63) Continuation of application No. 16/926,702, filed on Jul. 11, 2020, now Pat. No. 11,172,339.

(51) Int. Cl.
| | |
|---|---|
| *H04W 4/38* | (2018.01) |
| *C12Q 1/70* | (2006.01) |
| *C12Q 1/04* | (2006.01) |
| *G01S 19/39* | (2010.01) |
| *G01S 19/13* | (2010.01) |
| *G01N 33/483* | (2006.01) |
| *H04Q 9/00* | (2006.01) |
| *B64C 39/02* | (2023.01) |
| *G08B 21/12* | (2006.01) |
| *B64U 101/00* | (2023.01) |

(52) U.S. Cl.
CPC ............ *H04W 4/38* (2018.02); *B64C 39/024* (2013.01); *C12Q 1/04* (2013.01); *C12Q 1/70* (2013.01); *G01N 33/483* (2013.01); *G01S 19/13* (2013.01); *G01S 19/39* (2013.01); *G08B 21/12* (2013.01); *H04Q 9/00* (2013.01); *B64U 2101/00* (2023.01); *B64U 2201/104* (2023.01); *H04Q 2209/40* (2013.01); *H04Q 2209/50* (2013.01)

(58) Field of Classification Search
None
See application file for complete search history.

(56) References Cited

U.S. PATENT DOCUMENTS

| | | | |
|---|---|---|---|
| 10,592,510 B2* | 3/2020 | Amin | G06F 16/2455 |
| 10,821,202 B1* | 11/2020 | Chase | A61M 16/1065 |
| 11,007,292 B1* | 5/2021 | Grenon | A61L 2/24 |
| 11,172,339 B1* | 11/2021 | Hummer | H04W 4/38 |
| 2013/0311197 A1* | 11/2013 | Hummer | G06Q 30/0283 705/2 |
| 2015/0095301 A1* | 4/2015 | Amin | G06F 16/2455 707/706 |

(Continued)

FOREIGN PATENT DOCUMENTS

| | | | | |
|---|---|---|---|---|
| CN | 106885351 A | * | 6/2017 | |
| WO | WO-2012177807 A1 | * | 12/2012 | A61L 29/02 |

*Primary Examiner* — Fekadeselassie Girma
(74) *Attorney, Agent, or Firm* — Edmond DeFrank

(57) ABSTRACT

The embodiments disclose a method including using a monitor system for monitoring and detecting chemical compositions and biological pathogens, providing the monitor system configured to communicate with a cell phone, using at least one monitor/detector component, providing a plurality of biological sensors for detecting certain biological pathogens, and providing a plurality of chemical sensors for detecting certain chemical compositions.

20 Claims, 25 Drawing Sheets

(56) References Cited

U.S. PATENT DOCUMENTS

| | | | |
|---|---|---|---|
| 2016/0263261 A1* | 9/2016 | Trapani | A61L 2/202 |
| 2017/0028178 A1* | 2/2017 | Skoda | G16H 40/67 |
| 2020/0337594 A1* | 10/2020 | Reddy | G01N 33/57423 |

* cited by examiner

FIG. 20
↓

2100 — THE BIOLOGICAL PATHOGEN APP CAN BE CONFIGURED TO DETECT OR TRIGGER AN ALARM WHEN A PATHOGEN WHICH IS CONSIDERED HIGHLY INFECTIOUS IS DETECTED

2110 — THE BIOLOGICAL PATHOGEN APP IS CONFIGURED TO, ONCE A HIGHLY INFECTIOUS PATHOGEN IS DETECTED, SHARE THE DETECTION INFORMATION

2120 — FOR EXAMPLE, THE BIOLOGICAL PATHOGEN APP IS CONFIGURED TO USE THE COMMUNICATION CIRCUITRY TO BROADCAST AN ALERT (OR GENERATE A NOTIFICATION) VIA ANY SUITABLE COMMUNICATIONS NETWORK E.G., WIFI, NFC, BLUETOOTH, CELL, AND OTHER NETWORKS

2130 — THE ALERT MAY BE DIRECTLY SENT TO OTHER CELL PHONES AND/OR PERSONAL COMMUNICATION DEVICES IN THE AREA, OR MAY BE SENT TO A SERVER (OR THROUGH A NETWORK) AND THEN ON TO DEVICES WITHIN A RANGE OF A GIVEN LOCATION

2140 — THE BIOLOGICAL PATHOGEN APP IS CONFIGURED TO USE LOCATION INFORMATION FROM A GPS CHIP, WIFI OR ANY OTHER LOCATION INFORMATION AVAILABLE TO THE CELL PHONE TO IDENTIFY THE LOCATION OF THE DETECTED HIGHLY INFECTIOUS PATHOGEN

2150 — THE BIOLOGICAL PATHOGEN APP CAN BE CONFIGURED TO ALERT THE AUTHORITIES IN THE EVENT CERTAIN HIGHLY INFECTIOUS PATHOGENS ARE DETECTED

2160 — FOR EXAMPLE, THE DETECTION OF SARS-CoV-2 CAN TRIGGER INFORMATION RELATING TO THE LOCATION, TIME, AND OTHER DATA OF THE DETECTION TO BE FORWARDED TO CERTAIN DESIGNATED AUTHORITIES FOR PUBLIC HEALTH THREAT MANAGEMENT/MITIGATION

FIG. 21

METHOD AND DEVICES FOR DETECTING VIRUSES AND BACTERIAL PATHOGENS

CROSS-REFERENCE TO RELATED APPLICATIONS

This Patent Application is a Continuation and claims priority to United States Patent Application entitled: "METHOD AND DEVICES FOR DETECTING CHEMICAL COMPOSITIONS AND BIOLOGICAL PATHOGENS", U.S. Ser. No. 16/926,702 as filed on Jul. 11, 2020 filed by Gregory J. Hummer, the U.S. Patent Application being incorporated herein by reference.

BACKGROUND

The present exemplary embodiment relates to systems and methods for detecting chemicals. It finds particular application in conjunction with personal communication devices and/or other handheld or portable electronic devices and will be described with particular reference thereto. However, it is to be appreciated that the present exemplary embodiment is also amenable to other like applications.

Cargo containers are widely used for shipping materials by land or by water from one country to another. Knowing the contents of such containers has become of increasing importance in detecting potential threats. It has thus become extremely important to monitor the contents of such containers for harmful materials, such as explosives, harmful biological and chemical materials, and radiation materials.

BRIEF DESCRIPTION OF THE DRAWINGS

FIG. 21 shows a block diagram of an overview of communication circuitry to broadcast an alert of one embodiment.

DETAILED DESCRIPTION OF THE INVENTION

In a following description, reference is made to the accompanying drawings, which form a part hereof, and in which is shown by way of illustration a specific example in which the invention may be practiced. It is to be understood that other embodiments may be utilized and structural changes may be made without departing from the scope of the present invention.

General Overview:

It should be noted that the descriptions that follow, for example, in terms of a method and devices for detecting viruses and bacterial pathogens is described for illustrative purposes and the underlying system can apply to any number and multiple types of viruses and bacterial pathogens. In one embodiment of the present invention, the method and devices for detecting viruses and bacterial pathogens can be configured using one or both internal and external power source. The method and devices for detecting viruses and bacterial pathogens can be configured to include a single electrochemical sensing platform device and can be configured to include multiple electrochemical sensing platform devices using the present invention.

Figure 1:
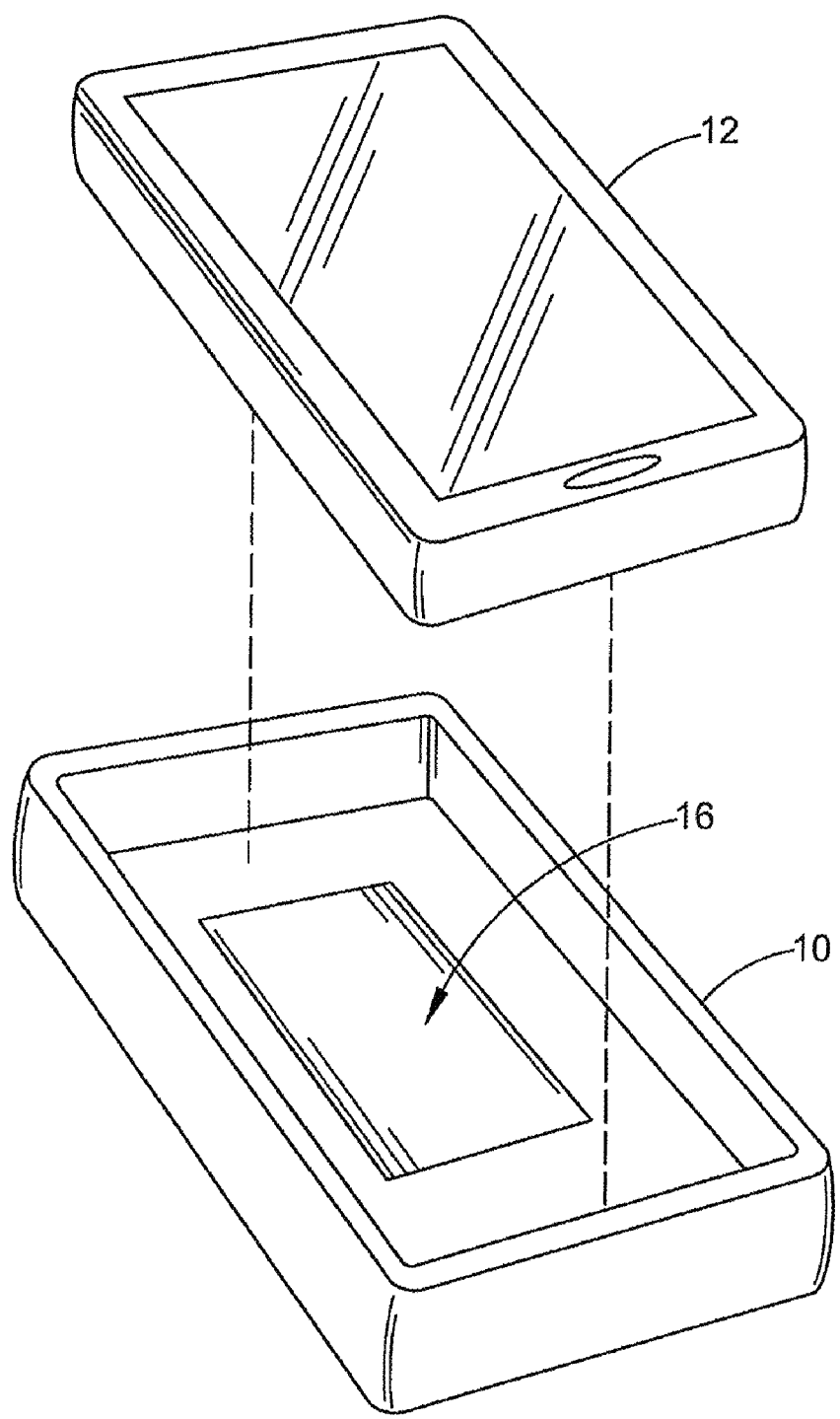
FIG. 1 illustrates a perspective view of an exemplary communication device and removable component in accordance with the present disclosure.

With reference to FIG. 1, an exemplary monitor for monitoring and detecting chemical compositions is illustrated and identified generally by reference numeral 10. In this embodiment, the monitor 10 is in the form of a protective case for a cell phone 12 or other personal communications device (e.g., tablets, laptops, etc.). It will be appreciated that the present disclosure is not limited to any particular case design or configuration, and that aspects of the disclosure can be embodied in a wide variety of both protective cases as well as ornamental cases and/or other devices attachable to either such cases or directly to a personal communication device. In other embodiments, aspects of the disclosure can be embodied in other types of accessories that may commonly be used with a cell phone or person communications device. For example wearable devices such as smart watches, peripheral devices such as Bluetooth speakers, etc.

Returning to FIG. 1, the cell phone 12 is configured to be received in and/or at least partially surrounded by the case 10 in any suitable fashion. In some arrangements, the case may be made of a resilient material that can be deformed to allow the cell phone 12 to be securely inserted and retained within the case. In other arrangements, the case can include a hard plastic two-piece frame between which the cell phone 12 is sandwiched. Again, a wide variety of case designs and types are envisioned. The case 10 further includes a monitor system, which in FIG. 1 is identified by reference numeral 16.

Figure 2:
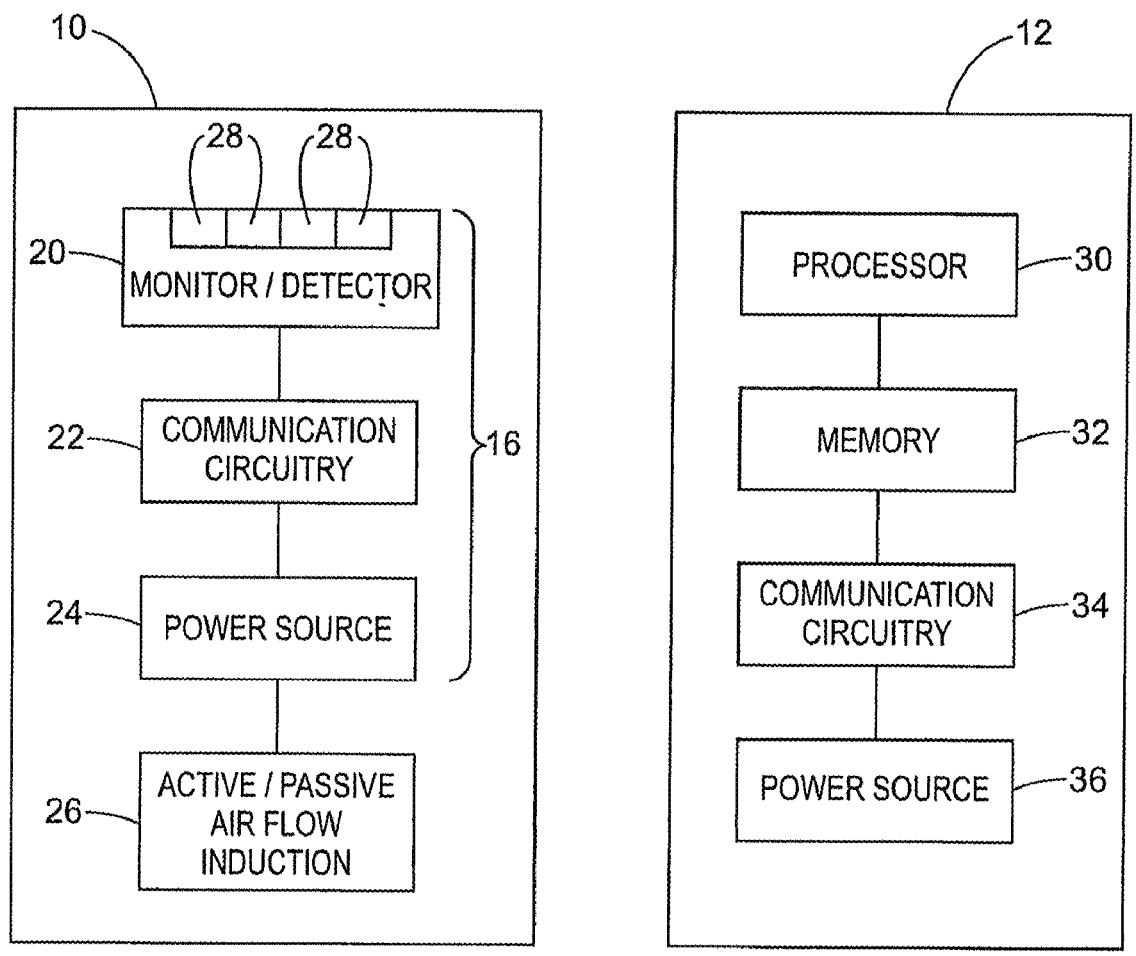
FIG. 2 illustrates a block diagram of an exemplary system in accordance with the present disclosure.

With reference to FIG. 2, the monitor system 16 generally includes a monitor/detector component 20. One monitor/detector component that is particularly well-suited for purposes of the present disclosure is set forth in U.S. Pat. No. 8,629,770 to Hummer et al. and U.S. Pat. No. 7,176,793 to Hummer, both of which are incorporated herein by reference in their entireties. Other types of monitor/detector components can also be used in accordance with the present disclosure.

The monitor system further includes communication circuitry 22 and a power source 24. The communication circuitry 22, in one embodiment, includes at least one of a near field communication device, Bluetooth communication device, WIFI communication device, or any other suitable communication circuity for establishing communications with the cell phone 12. The power source 24 can be a power supply such as a battery (lithium or other) mounted or otherwise contained within case 10. In other embodiments, the power source 24 can be an antenna configured to receive energy wirelessly and supply the received energy to one or both of the monitor/detector component 20 and/or communication circuitry 22 such that no onboard battery is required for operation of the monitor system 16. In still other arrangements, the power source 24 can be a connector configured to couple with a port of the cell phone 12 to receive power from a power source of the cell phone 12.

An active or passive air flow induction device 26 can be provided for ensuring adequate and or continuous flow of air to the monitor 20. Such devices can include fans, micropumps, louvers, vents etc. An active induction device can be separately replaceable within the system and can include its own power supply. Alternatively, an active induction device can be configured to receive power from power supply 24.

It should be appreciated that the monitor/detector component 20 can comprise a plurality of sensors 28. The sensors 28 can be individually replaceable or can be replaced as a unit. Replacement of the sensors may be necessary due to sensor degradation. In other situations, a user may wish to detect certain chemicals and will choose which sensors to install in the system. In one embodiment, the entire monitor system 16 is replaceable as a unit.

The sensors 28 may detect harmful materials, such as explosives, radioactive materials, harmful chemicals, such as chemical warfare agents, nerve gases, biological materials, such as gases, anthrax and other germ warfare agents, narcotics and other illegal drugs, or combinations thereof. At least one of the sensors 28 can be configured for generating a signal which is indicative of the presence of a nitrogen-based explosive, such as trinitrotoluene (TNT) and/or a peroxide based explosive, such as triacetone triperoxide (TATP) or hexamethylenetriperoxidediamine (HMTD), or a combination thereof, for example.

It will be appreciated that the monitor system 16 is configured to communicate with the cell phone 12. That is, the monitor system 16 collects data and transmits or otherwise shares the collected data with the cell phone 12 for processing. The cell phone 12 of the illustrated embodiment includes a processor 30, a memory 32, a communication circuitry 34, and a power source 36. It will be appreciated that the cell phone 12 can include a wide variety of additional components as is conventional. Such additional components can include a display device, input device, various sensors, various antennas, etc.

Data collected by the monitor/detector 20 is transmitted via communication circuitry 22 to communication circuitry 34 of the cell phone 12. Other data, such as sensor state, status, performance data, and the like can also be transmitted to the cell phone 12. Any suitable manner of transmitting the data from the monitor system 16 to the cell phone 12 can be employed.

The data collected and transmitted by the monitoring system 16 is then processed by the phone to detect one or more chemicals in accordance with one or more methods set forth in U.S. Pat. No. 8,629,770 to Hummer et al. and U.S. Pat. No. 7,176,793 to Hummer. To this end, suitable software for analyzing the data is stored in memory 32 of the cell phone 12. Other detection and/or analyzing methods and techniques may also be used in conjunction with aspects of the present disclosure.

In one embodiment, the software stored in memory 12 can be in the form of an application, or "app", that is downloaded from an app store or the like. The app can be provided with various "signatures" of chemicals. The signatures can be compared to the data to determine whether the chemical signature was detected by the monitoring system 16. The app can be configured to be automatically updated with new signatures as the need to detect particular chemicals arise. That is, it is possible to provide new and/or additional chemical signatures for the app to check against the data to detect specific chemicals.

The app can further include features such as adjustable thresholds. For example, for some chemicals that are routinely present in certain amounts and/or not generally considered dangerous below certain levels, the application can be configured to detect or trigger an alarm when a threshold amount is met or exceeded. For some chemicals which are considered dangerous in any amount, the thresholds would not generally be adjustable.

The app can be further configured to, once a chemical is detected, share the detection information. For example, the application can be configured to use the communication circuitry 34 to broadcast an alert (or generate a notification) via any suitable communications network (e.g., WIFI, NFC, Bluetooth, cell, etc.). The alert may be directly sent to other cell phones and/or personal communication devices in the area or may be sent to a server (or through a network) and then on to devices within a range of a given location. Accordingly, the application can be configured to use location information from a GPS chip, WIFI or any other location information available to the cell phone 12 to identify the location of the detected chemical.

The app can be configured to alert the authorities in the event certain chemicals are detected. For example, the detection of any amount of sarin gas (or other chemical/biological weapon) can trigger information relating to the location, time, etc. of the detection to be forwarded to certain designated authorities for threat management/mitigation.

It should be appreciated that a network of devices having monitoring systems, each detecting a certain chemical, can be configured to share valuable data regarding the dispersion of the particular chemical. For example, devices in close proximity to each other and the point of origin of the chemical may detect a greater concentration of the chemical than devices further away from the point of origin. Using this data and an appropriate dispersion model, a point of origin can be calculated. This can allow responsive action to be taken more quickly than otherwise would be the case.

Similarly, the data (location, concentration, etc.) from a plurality of such devices can be used to predict dispersion of the chemical so that preemptive action can be taken to minimize exposure of humans to the detected chemical.

Providing the monitoring system 16 in a separate component that is attachable to a phone or other personal communication device has several advantages. For example, any and all such devices can become monitors/detectors upon the provision of a suitable case or other component. Accordingly, a consumer can decide whether to add the functionality. In addition, the orientation, location and other aspects of the positioning of the sensor elements within the case or other component can be standardized to provide more consistent detection as compared to placing the sensor elements within various different models of cell phones. This is because the myriad phone manufacturers and models each have different space constraints that would dictate different available locations, orientations, etc. for the sensor elements within the phone. As such, some sensor elements would be in a better position within a respective phone to detect chemicals than other phones. This can lead to widely varying detection accuracy between different phones exposed to the same concentration of a given chemical.

It should be appreciated that, although the monitoring system 16 is illustrated as part of a case 10, the monitoring system can also be provided as a separate unit attachable either directly to a cell phone or the like, or attachable to a case in which a cell phone is contained.

Figure 3:
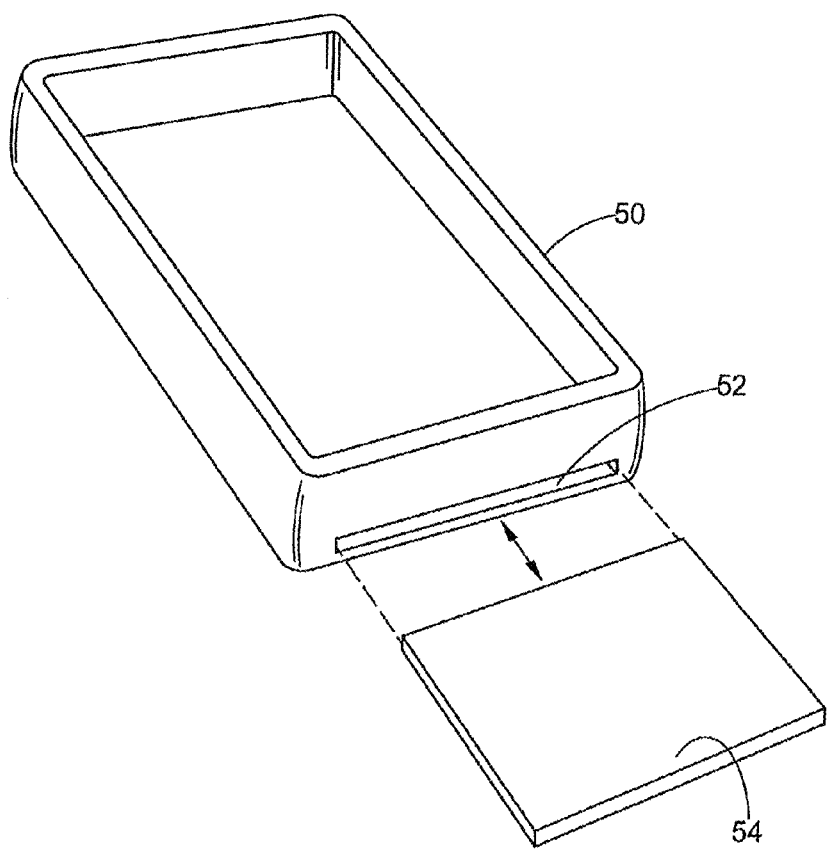
FIG. 3 illustrates another exemplary removable component in accordance with the present disclosure.

With reference to FIG. 3, another exemplary embodiment is illustrated and includes a case for a personal communication device identified generally by reference numeral 50. In this embodiment, the case 50 is similar to the case 10 of FIG. 1 but further includes a slot 52 for receiving a removable and/or replaceable monitoring system 54. In one embodiment, the removable/replaceable component 55 includes all of the components of the monitoring system such as a power source, monitor/detector components, and communications circuitry. In other embodiments, the removable/replaceable component can include only the sensors of the monitor/detector, only the power source, only the communication circuitry, or any combination thereof. The removable/replaceable component can be configured to "click-lock" in the slot 52 in a manner similar to an SD card or the like wherein the component is pressed into the slot until a latch engages to retain the component and then pressed further into the slot to release the latch for removal. It will be appreciated that there are a wide variety of ways to retain the removable component in the slot. A seal or weatherproof cap can be provided to prevent ingress of water or contaminants.

While the foregoing embodiments illustrate a monitoring system attachable to a personal communication device directly or via a protective case or the like, it should be appreciated that the monitoring system of the above described embodiments can also link to the personal communication device without being physically attached thereto. Thus, the monitoring system can be provided as a standalone system to which the personal communication device can be configured to connect to perform the above described functions.

Figure 4:
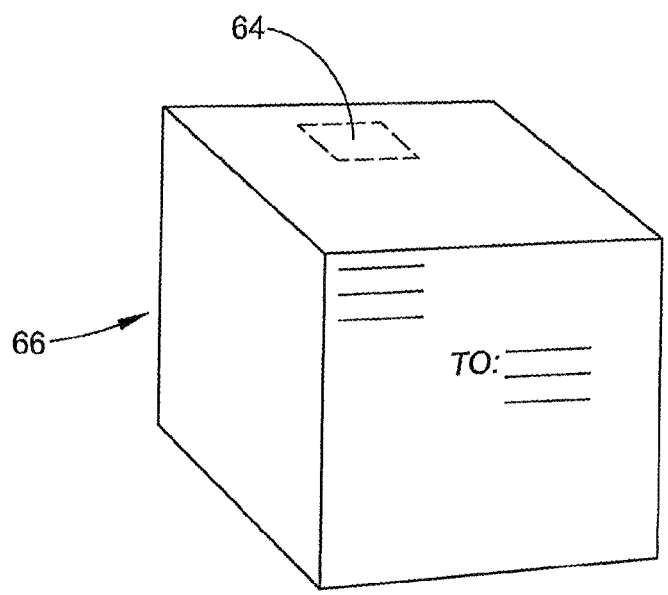
FIG. 4 illustrates an exemplary container including a monitoring system in accordance with the present disclosure.

For example, with reference to FIG. 4, a monitoring system 64 is provided in a separate container 66, such as a shipping box or the like. When the personal communication device is placed in proximity to the shipping box, the monitoring system can be configured to connect a personal communication device, such as cell phone 12, and perform the above-described functionality. The monitoring system can be placed inside the box, for detecting chemicals carried within the box, for example. In other embodiments the monitoring system 64 can additionally or alternatively monitor for chemicals outside of the box.

It should be appreciated that the monitoring system 64 can be configured to communicate with other devices besides (or in addition to) the personal communication device described above. Such devices can include scanners or other devices adapted to connect and receive data from a plurality of such monitoring systems disposed in a plurality of respective containers.

In one example, a scanning device can be associated with a conveyor system of a parcel service for scanning packages by communicating with monitoring systems associated with the packages as they advance through a shipping facility. In another example, the monitoring devices of the present disclosure can be associated with luggage (or other airline or common carrier freight). It will be appreciated that a wide variety of applications for the technology of the present disclosure are contemplated.

In some embodiments, it can be advantageous to include active and/or passive air flow inducing devices for ensuring sufficient air flow across the sensors.

This can be particularly advantageous for applications wherein the sensors are in a fixed location, such as within a cargo hold or other location. Suitable devices can include fans or micropumps for displacing air across and/or adjacent a sensor installation. In some applications, louvers or vent openings can be positioned to maximize air flow to the sensor. Increasing air flow can make detection of certain chemicals more efficient.

It should be appreciated that the monitoring system 16 of the present disclosure can be configured to activate sensors 28 only when connected to a personal communication device or the like. In such configuration, the monitoring system generally lies dormant until such time as a connection is made with a remote device. The system 16 may then begin sensing for one or more chemicals and transmitting data to the remote device.

In another configuration, the system 16 may be configured to periodically activate to sense for the presence of one or more chemicals regardless of whether the system 16 is connected to a remote device. In this case, once the system 16 connects to a remote device, all past data gathered by the system 16 can be transmitted to the remote device to provide a sensing history.

Figure 5:
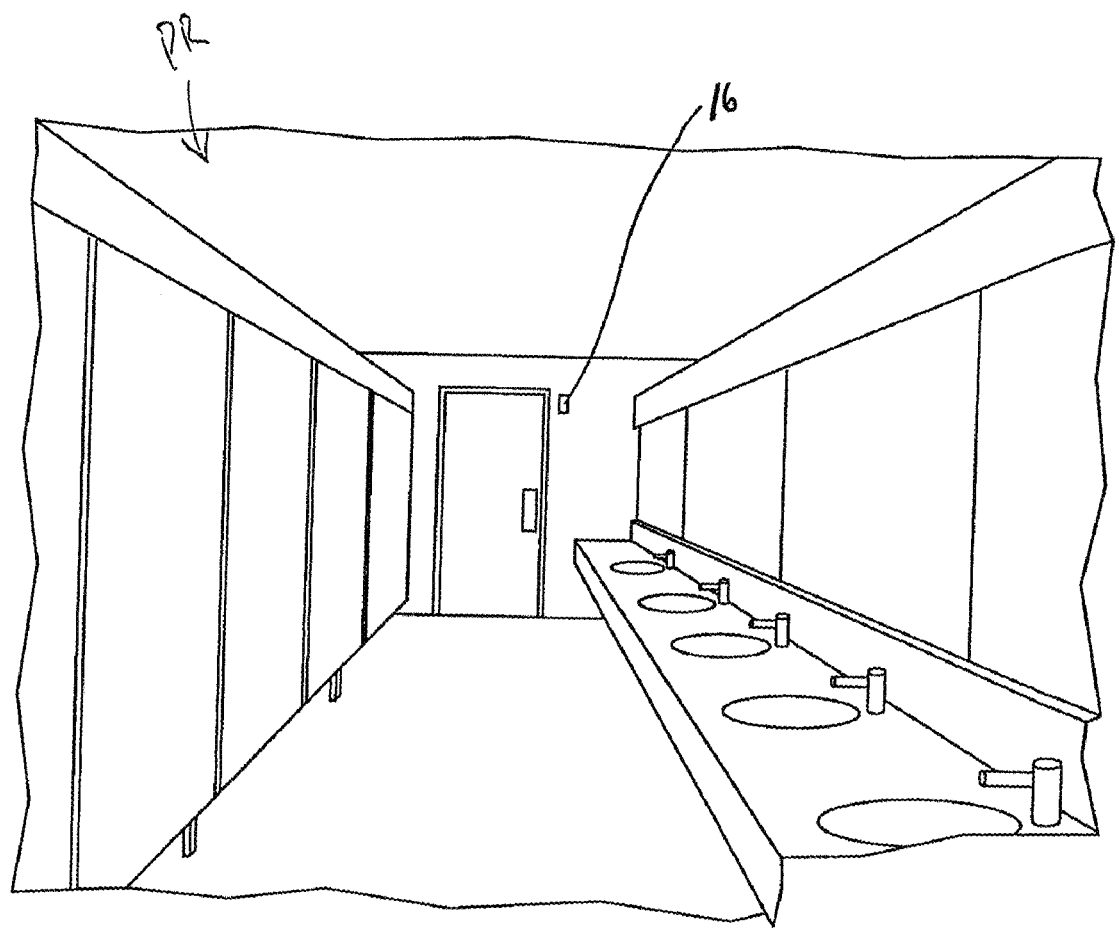
FIG. 5 illustrates an exemplary public space in which the monitoring system in accordance with the present disclosure is configured to monitor.

Turning to FIGS. 5-9, various applications of the exemplary monitoring system are illustrated. In FIG. 5, a monitoring system 16 is deployed in a public restroom facility PR. The monitoring system 16 can be placed near a door in a position to where air flow into/out of the facility may generally be optimized. The monitoring system 16 could also be incorporated into an exhaust air duct of the facility. The monitoring system 16 can be configured to communicate with one or more handheld devices or can establish a permanent or semi-permanent connection to existing communication infrastructure, such as WIFI or the like.

Figure 6:
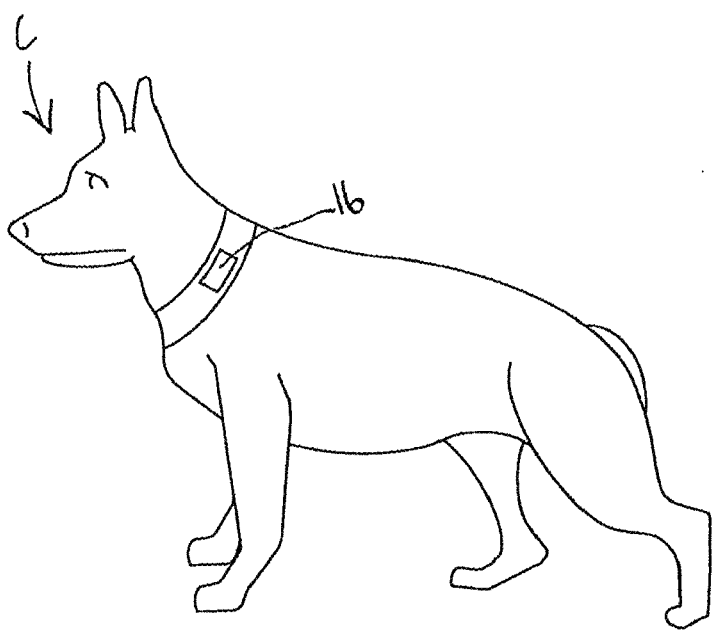
FIG. 6. illustrates an exemplary monitoring system in accordance with the present disclosure integrated into a collar of a law enforcement canine.

In FIG. 6, a monitoring system 16 is integrated into the collar of a law enforcement canine C. It will be appreciated that movement of the canine C will cause air to circulate around the monitoring system 16 to enhance sensing capabilities. In addition, the canine can be instructed to enter certain spaces for inspection and/or sampling of the air that would generally not be accessible by other methods. In addition to mounting on a canine, the monitoring system can be mounted on other mobile platforms such as drones or unmanned or manned vehicles.

Figure 7:
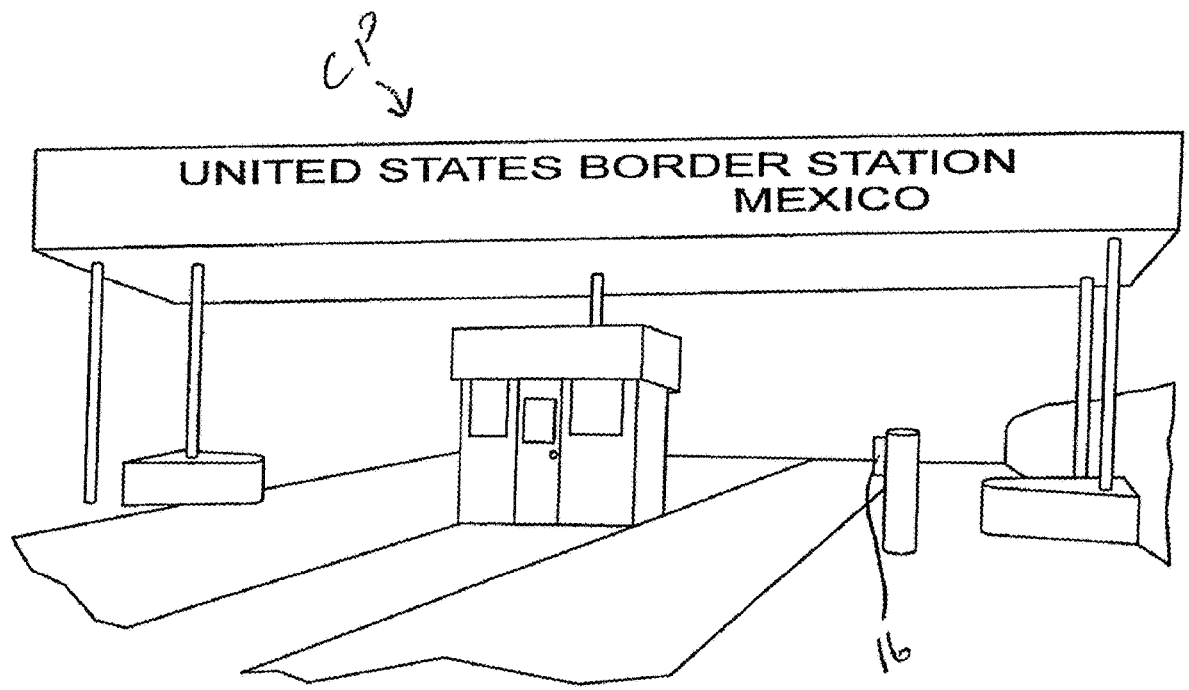
FIG. 7 illustrates another exemplary public space in which the monitoring system in accordance with the present disclosure is configured to monitor.

FIG. 7 illustrates a monitoring system 16 in a customs and/or border patrol checkpoint CP. It will be appreciated a plurality of monitoring systems can be deployed in suitable locations throughout the checkpoint. In the illustrated embodiment, the monitoring system is shown on a post adjacent a vehicle travel path.

Figure 8:
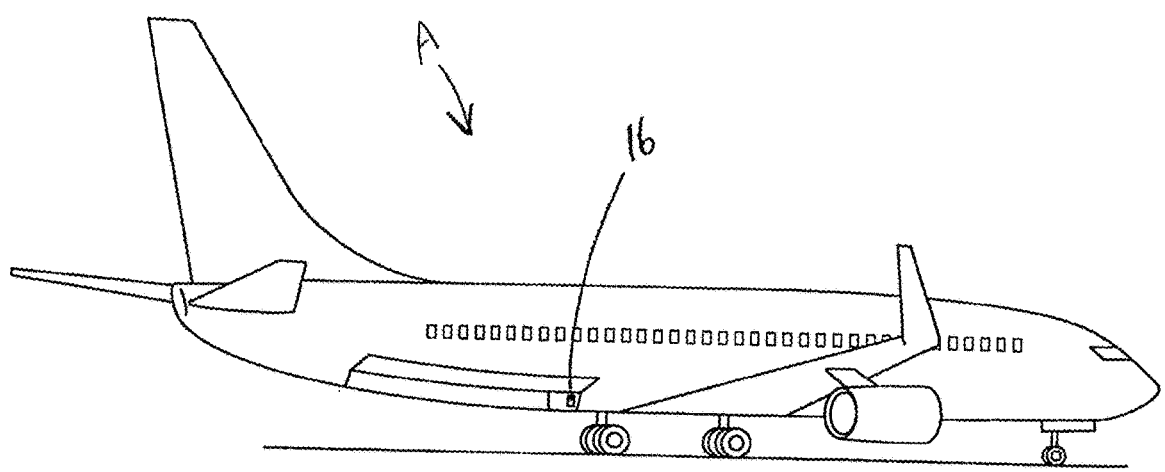
FIG. 8 illustrates an exemplary monitoring system in accordance with the present disclosure integrated into a cargo hold of an aircraft.

FIG. 8 illustrates a monitoring system 16 in a cargo hold of an aircraft A, such as a commercial airliner.

Figure 9:
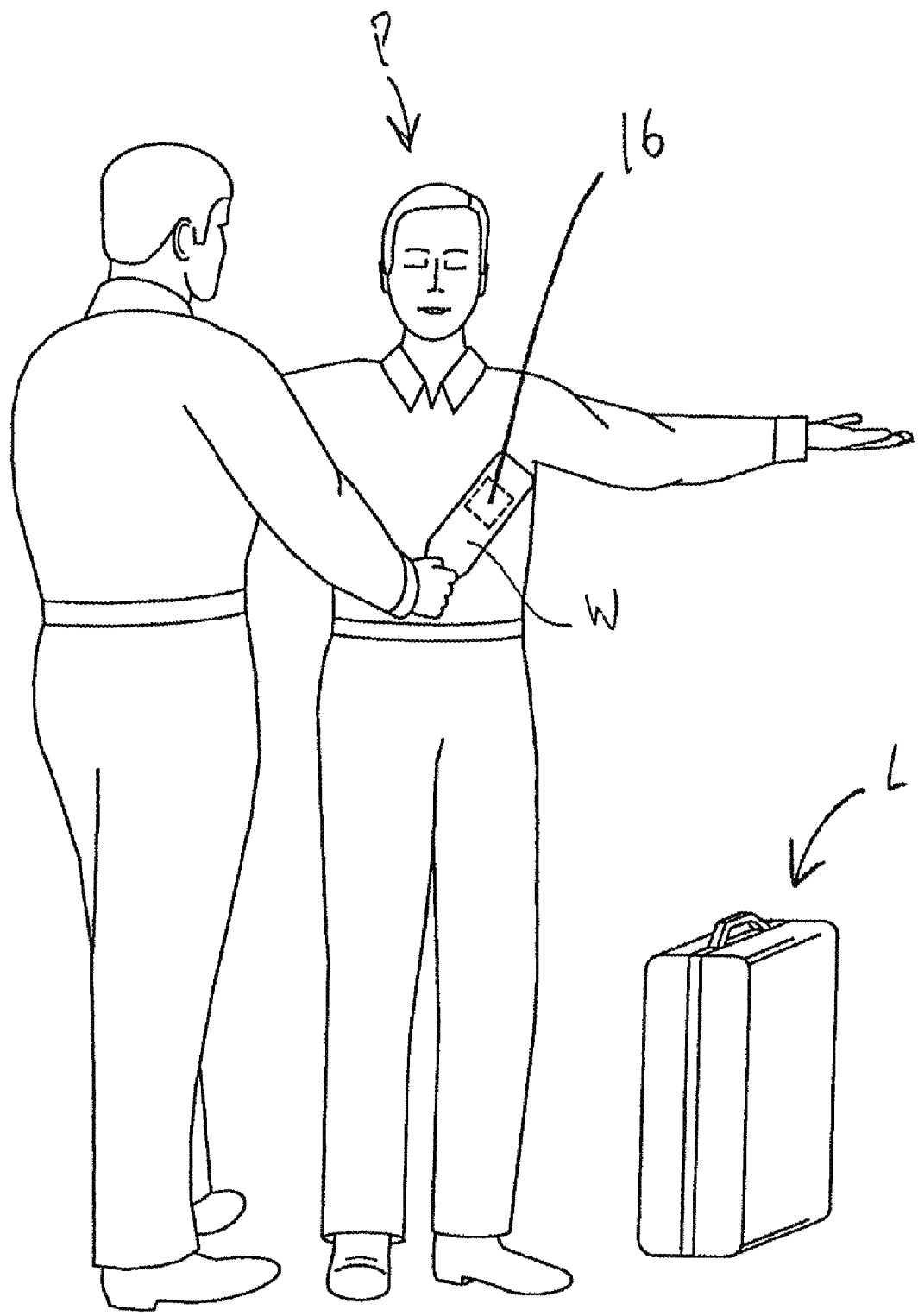
FIG. 9 illustrates an exemplary monitoring system in accordance with the present disclosure integrated into a handheld wand for scanning passengers and/or luggage.

FIG. 9 illustrates a monitoring system 16 integrated into a handheld wand W for manually scanning/sampling a passenger P and the passenger's luggage L. It will be appreciated that the monitoring system 16 can be incorporated into existing wands, such as metal detector wands typically used by security personnel for scanning passengers at airports or other individuals.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

Figure 10:
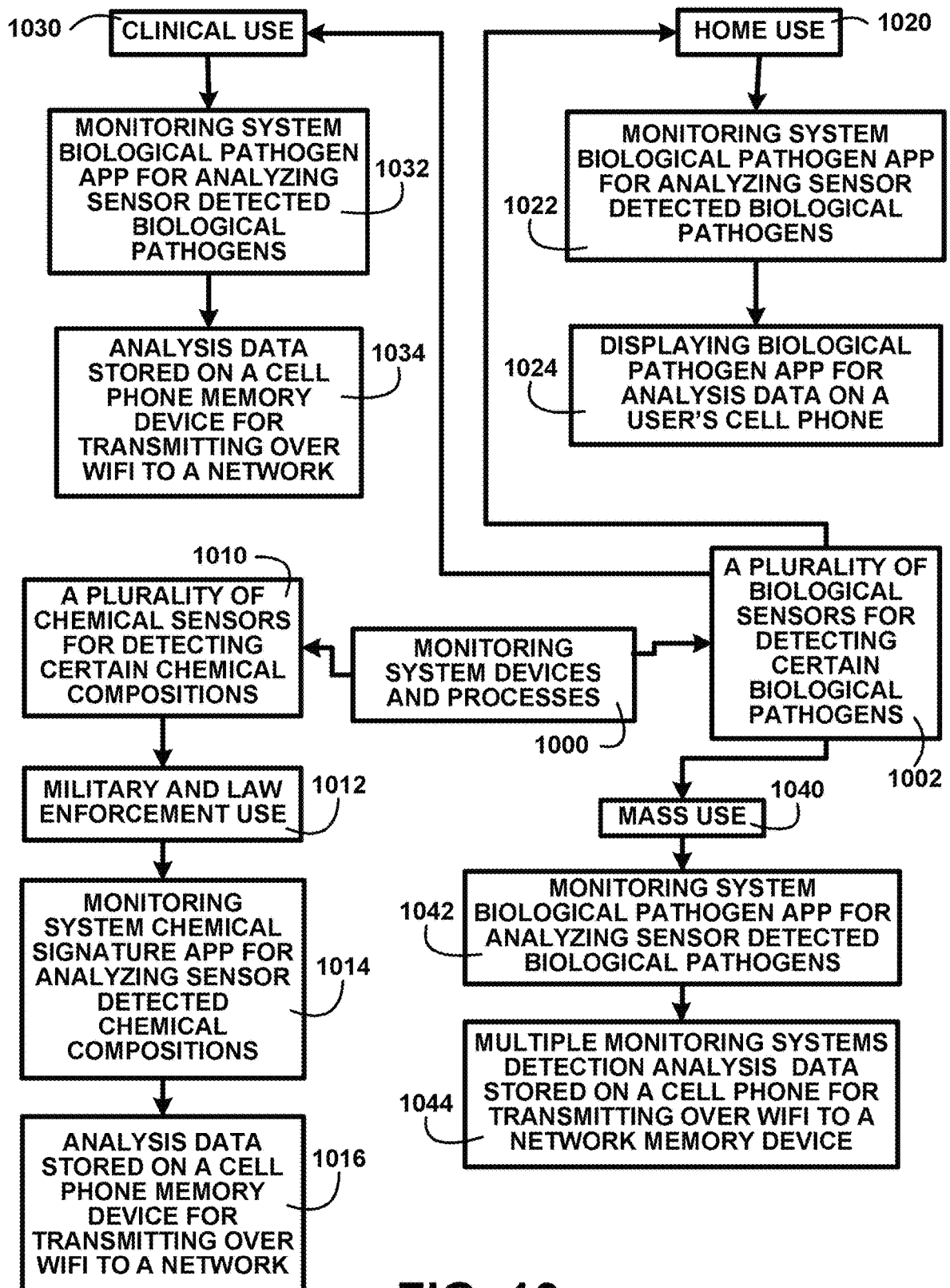
FIG. 10 shows a block diagram of an overview of a monitoring system devices and processes of one embodiment.

Monitoring System Devices and Processes:

FIG. 10 shows a block diagram of an overview of monitoring system devices and processes of one embodiment. FIG. 10 shows monitoring system devices and processes 1000 including a plurality of chemical sensors for detecting certain chemical compositions 1010. In one embodiment the plurality of chemical sensors for detecting certain chemical compositions 1010 are applied for military and law enforcement use 1012. A monitoring system chemical signature app for analyzing sensor detected chemical compositions 1014 is also used for analysis data stored on a cell phone memory device for transmitting over WIFI to a network 1016.

FIG. 10 shows a plurality of biological sensors for detecting certain biological pathogens 1002. In one embodiment the plurality of biological sensors for detecting certain biological pathogens 1002 is applied for home use 1020. A monitoring system biological pathogen app for analyzing sensor detected biological pathogens 1022 and for displaying biological pathogen app for analysis data on a user's cell phone 1024.

In another embodiment a monitoring system biological pathogen app for analyzing sensor detected biological pathogens 1032 is applied for clinical use 1030. The analysis data stored on a cell phone memory device for transmitting over WIFI to a network 1034. In yet another embodiment a mass use 1040 uses a monitoring system biological pathogen app for analyzing sensor detected biological pathogens 1042. Also uses multiple monitoring systems detection analysis data stored on a cell phone for transmitting over WIFI to a network memory device 1044 of one embodiment.

Figure 11:
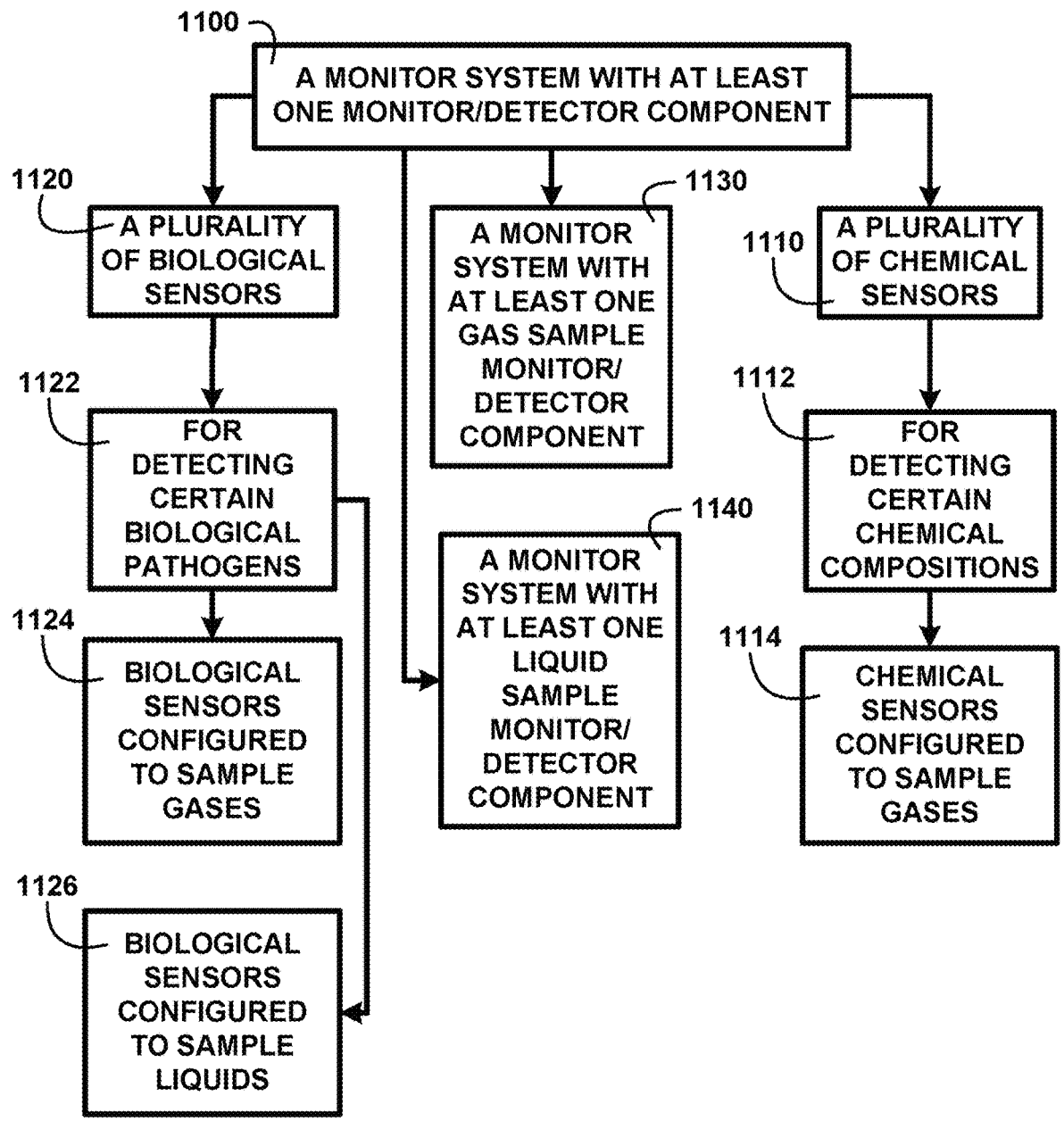
FIG. 11 shows a block diagram of an overview of a monitor/detector component of one embodiment.

Monitor/Detector Component:

FIG. 11 shows a block diagram of an overview of monitor/detector component of one embodiment. FIG. 11 shows a monitor system with at least one monitor/detector component 1100 with a plurality of chemical sensors 1110 for detecting certain chemical compositions 1112. The plurality of chemical sensors 1110 includes chemical sensors configured to sample gases 1114. The monitor system with at least one monitor/detector component 1100 can be configured with a plurality of biological sensors 1120 for detecting certain biological pathogens 1122. The plurality of biological sensors 1120 includes biological sensors configured to sample gases 1124. The plurality of biological sensors 1120 includes biological sensors configured to sample liquids 1126. The devices include a monitor system with at least one gas sample monitor/detector component 1130. The devices include a monitor system with at least one liquid sample monitor/detector component 1140 of one embodiment.

Figure 12:
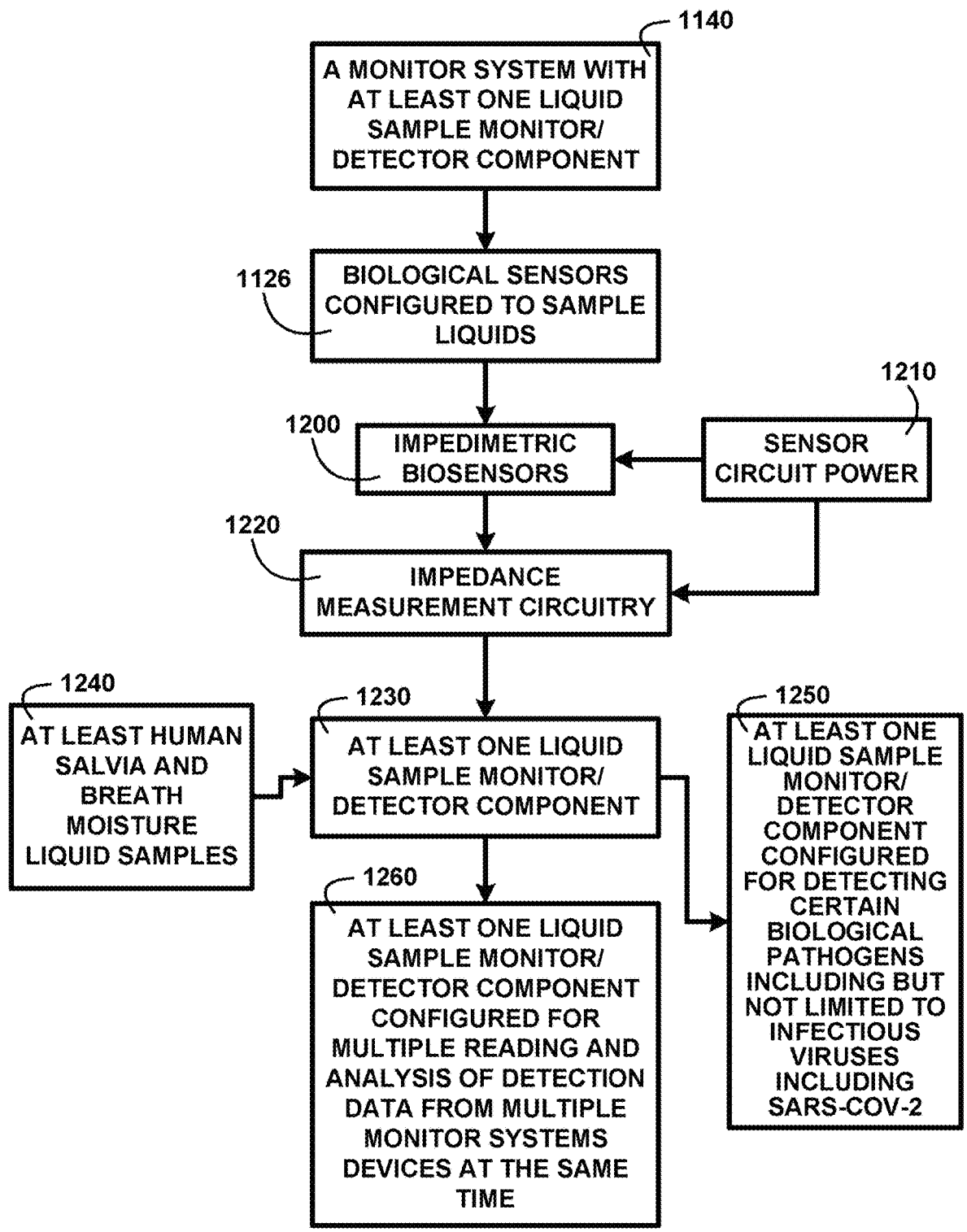
FIG. 12 shows a block diagram of an overview of a liquid sample monitor/detector component of one embodiment.

Liquid Sample Monitor/Detector Component:

FIG. 12 shows a block diagram of an overview of liquid sample monitor/detector component of one embodiment. FIG. 12 shows a monitor system with at least one liquid sample monitor/detector component 1140 with biological sensors configured to sample liquids 1126. Detection using liquid samples is preformed using impedimetric biosensors 1200. The impedimetric biosensors 1200 are powered using sensor circuit power 1210 and use impedance measurement circuitry 1220 for an analysis process. At least one liquid sample monitor/detector component 1230 is configured for at least human salvia and breath moisture liquid samples 1240.

At least one liquid sample monitor/detector component configured for detecting certain biological pathogens including but not limited to infectious viruses including SARS-CoV-2 1250. In another embodiment at least one liquid sample monitor/detector component configured for multiple reading and analysis of detection data from multiple monitor systems devices at the same time 1260 of one embodiment.

Figure 13:
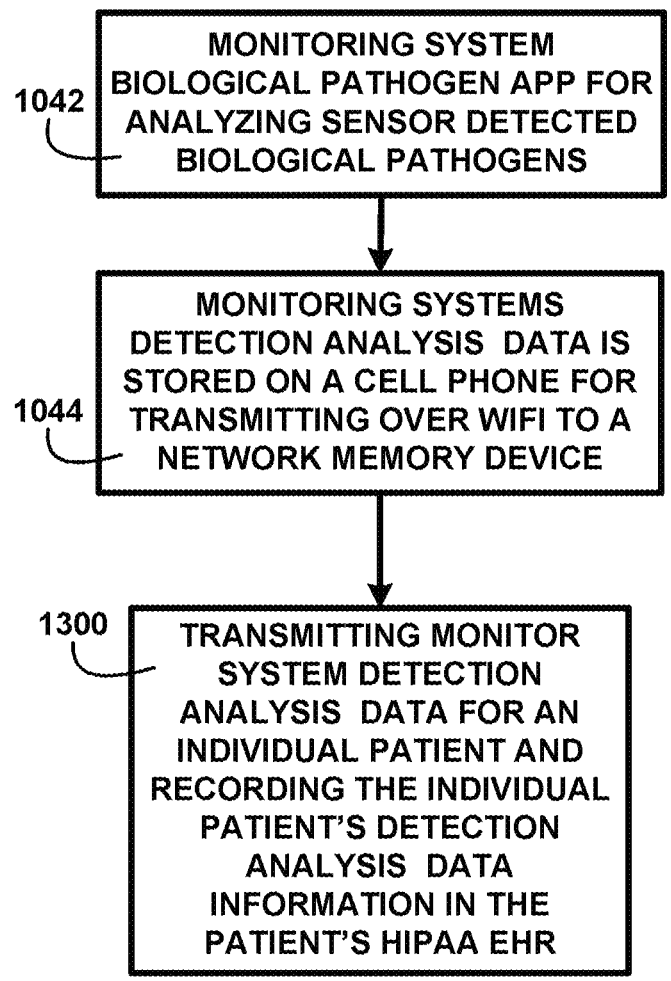
FIG. 13 shows a block diagram of an overview of recording the individual patient's detection analysis data information in the patient's HIPAA EHR of one embodiment.

Recording the Individual Patient'S Detection Analysis Data Information in the Patient's HIPAA EHR:

FIG. 13 shows a block diagram of an overview of recording the individual patient's detection analysis data information in the patient's HIPAA EHR of one embodiment. FIG. 13 shows monitoring system biological pathogen app for analyzing sensor detected biological pathogens 1042. Monitoring systems detection analysis data is stored on a cell phone for transmitting over WIFI to a network memory device 1044. The process includes transmitting monitor system detection analysis data for an individual patient and recording the individual patient's detection analysis data information in the patient's HIPAA EHR 1300 of one embodiment.

Figure 14:
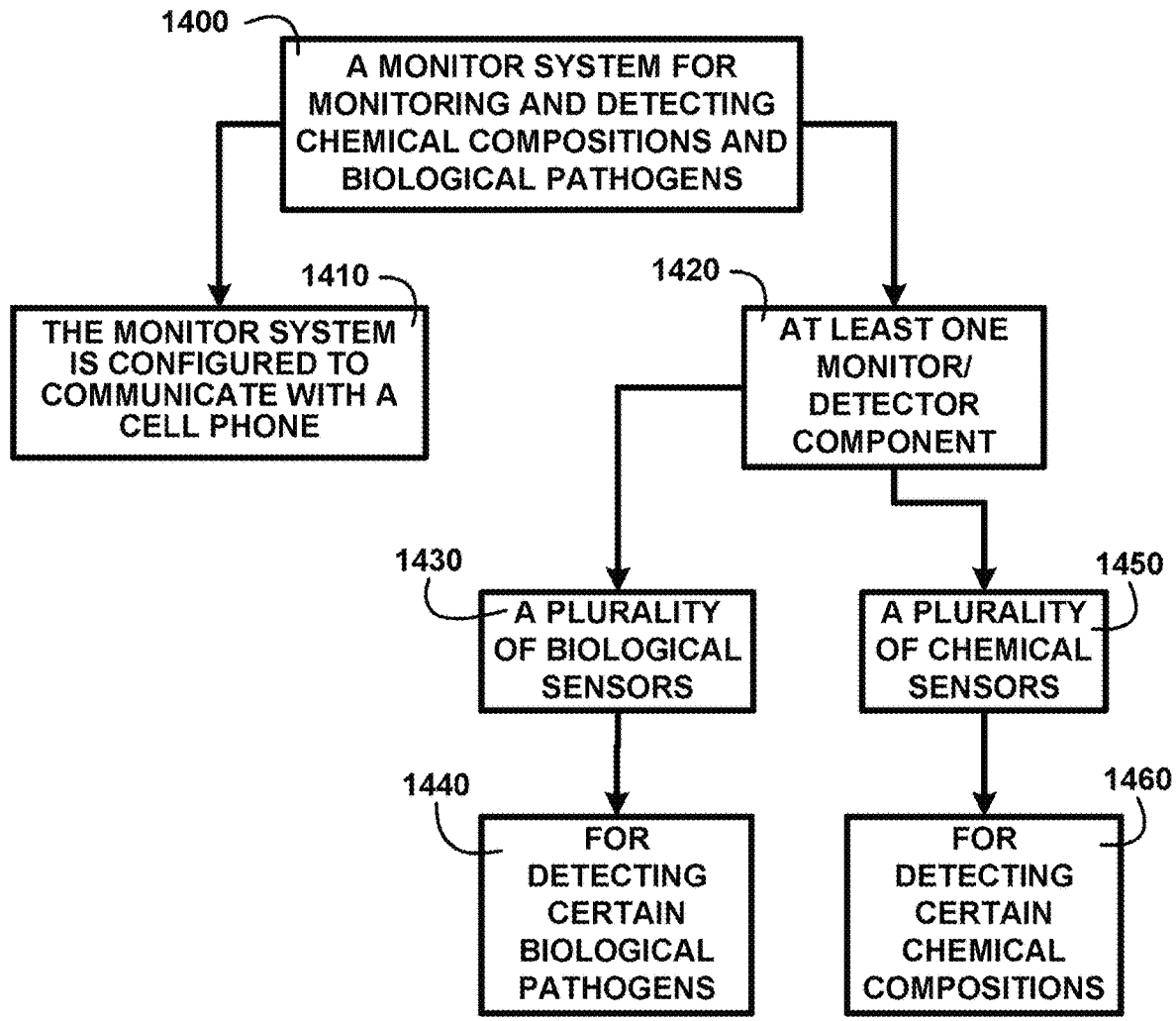
FIG. 14 shows a block diagram of an overview of a monitor system for monitoring and detecting chemical compositions and biological pathogens of one embodiment.

A Monitor System for Monitoring and Detecting Chemical Compositions and Biological Pathogens:

FIG. 14 shows a block diagram of an overview of a monitor system for monitoring and detecting chemical compositions and biological pathogens of one embodiment. FIG. 14 shows a monitor system for monitoring and detecting chemical compositions and biological pathogens 1400. The monitor system is configured to communicate with a cell phone 1410. The monitor system is configured with at least one monitor/detector component 1420. The monitor system is configured with a plurality of biological sensors 1430 for detecting certain biological pathogens 1440. The monitor system is configured with a plurality of chemical sensors 1450 for detecting certain chemical compositions 1460 of one embodiment.

Figure 15:
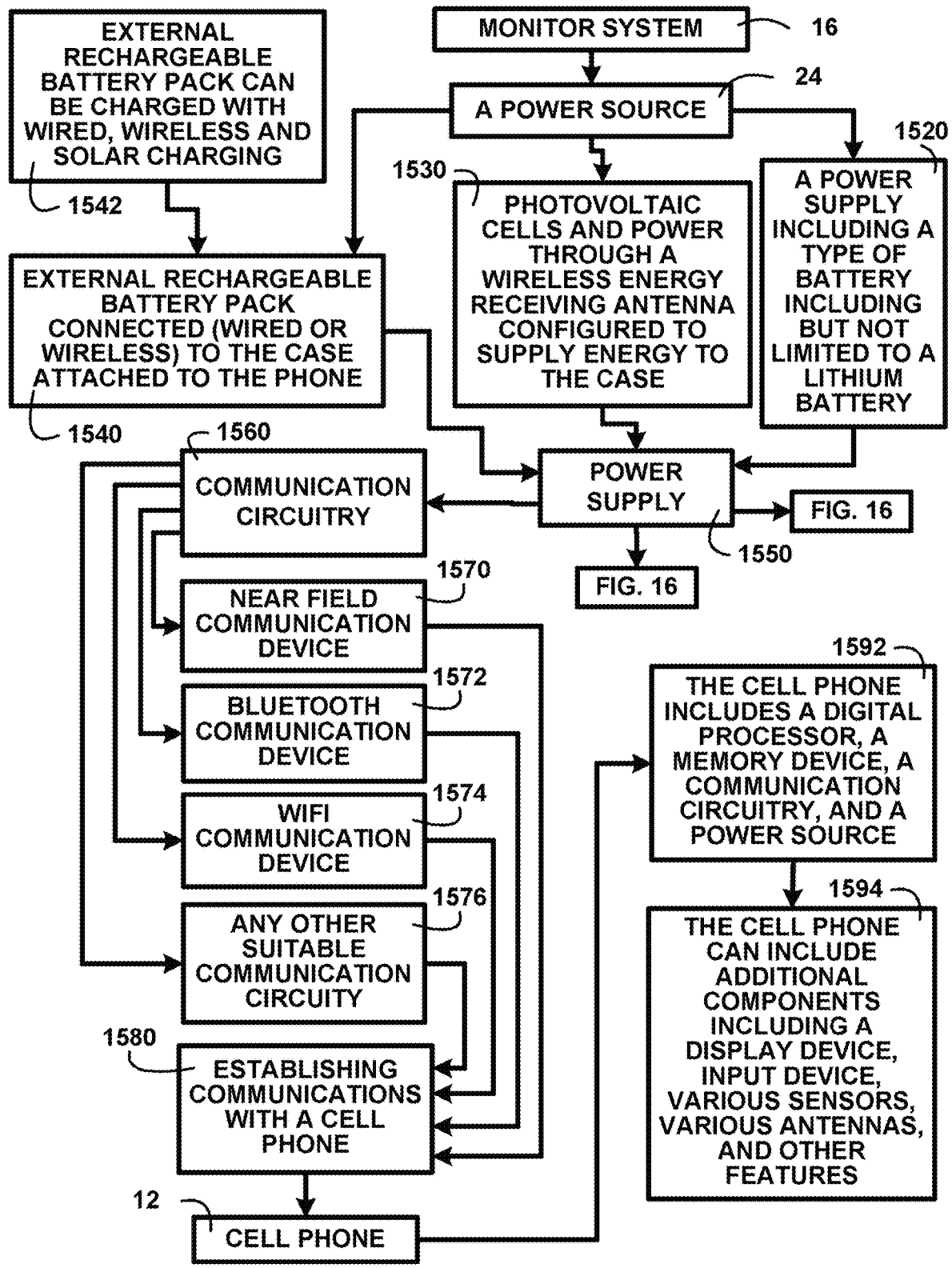
FIG. 15 shows a block diagram of an overview of a power source of one embodiment.

A Power Source:

FIG. 15 shows a block diagram of an overview of a power source of one embodiment. FIG. 15 shows the monitor system 16 coupled to a power source 24. The power source 24 can be configured to include a power supply including a type of battery including but not limited to a lithium battery 1520. The power source 24 can be configured to include photovoltaic cells and power through a wireless energy receiving antenna configured to supply energy to the case 1530. The power source 24 can be configured to include a external rechargeable battery pack connected (wired or wireless) to the case attached to the phone 1540. The external rechargeable battery pack can be charged with wired, wireless and solar charging 1542.

Figure 16:
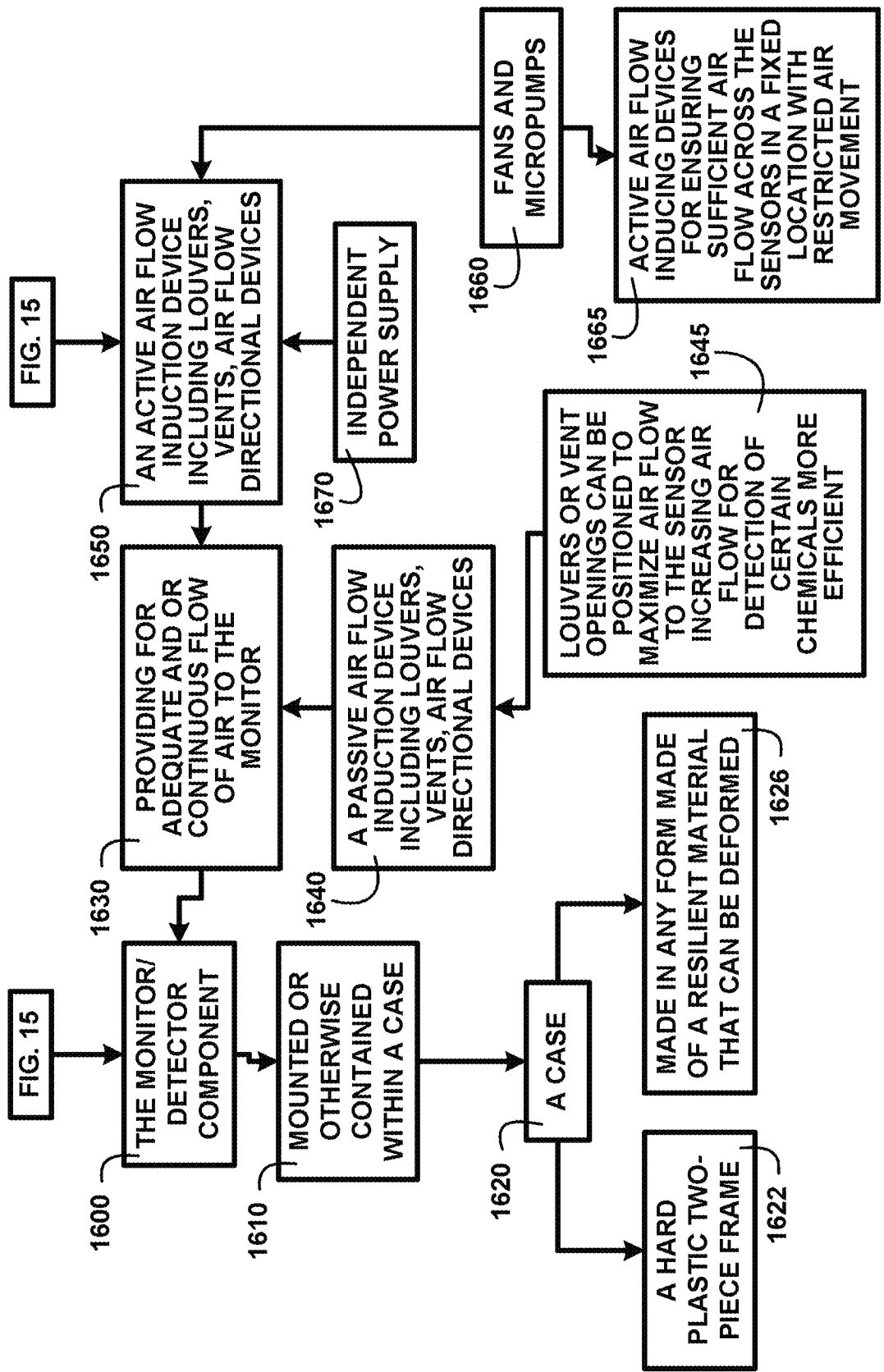
FIG. 16 shows a block diagram of an overview of an air flow induction device of one embodiment.

The power source 24 is configured to be a power supply 1550 as shown in FIG. 16. The power source 24 is configured to be a power supply 1550 for communication circuitry 1560. Communication circuitry 1560 can be configured to include one or more from a group including a near field communication device 1570, Bluetooth communication device 1572, WIFI communication device 1574 and any other suitable communication circuity 1576. The communication circuitry 1560 is used for establishing communications with a cell phone 12. A cell phone 12 or other communication device is the communication link to the user. The cell phone includes a digital processor, a memory device, a communication circuitry, and a power source 1592. The cell phone can include additional components including a display device, input device, various sensors, various antennas, and other features 1594 of one embodiment.

An Air Flow Induction Device:

FIG. 16 shows a block diagram of an overview of an air flow induction device of one embodiment. FIG. 16 shows a continuation from FIG. 15 the monitor/detector component 1600 mounted or otherwise contained within a case 1610. A case 1620 can be made of a hard plastic two-piece frame 1622. A case 1620 can be made in any form made of a resilient material that can be deformed 1626. An air flow induction device is used for providing for adequate and or continuous flow of air to the monitor 1630. A passive air flow induction device including louvers, vents, air flow directional devices 1640. Louvers or vent openings can be positioned to maximize air flow to the sensor increasing air flow for detection of certain chemicals more efficient 1645.

Also continuing from FIG. 15 is showing an active air flow induction device including louvers, vents, air flow directional devices 1650 with an independent power supply 1670, fans and micro pumps 1660 and active air flow inducing devices for ensuring sufficient air flow across the sensors in a fixed location with restricted air movement 1665 of one embodiment.

Figure 17:
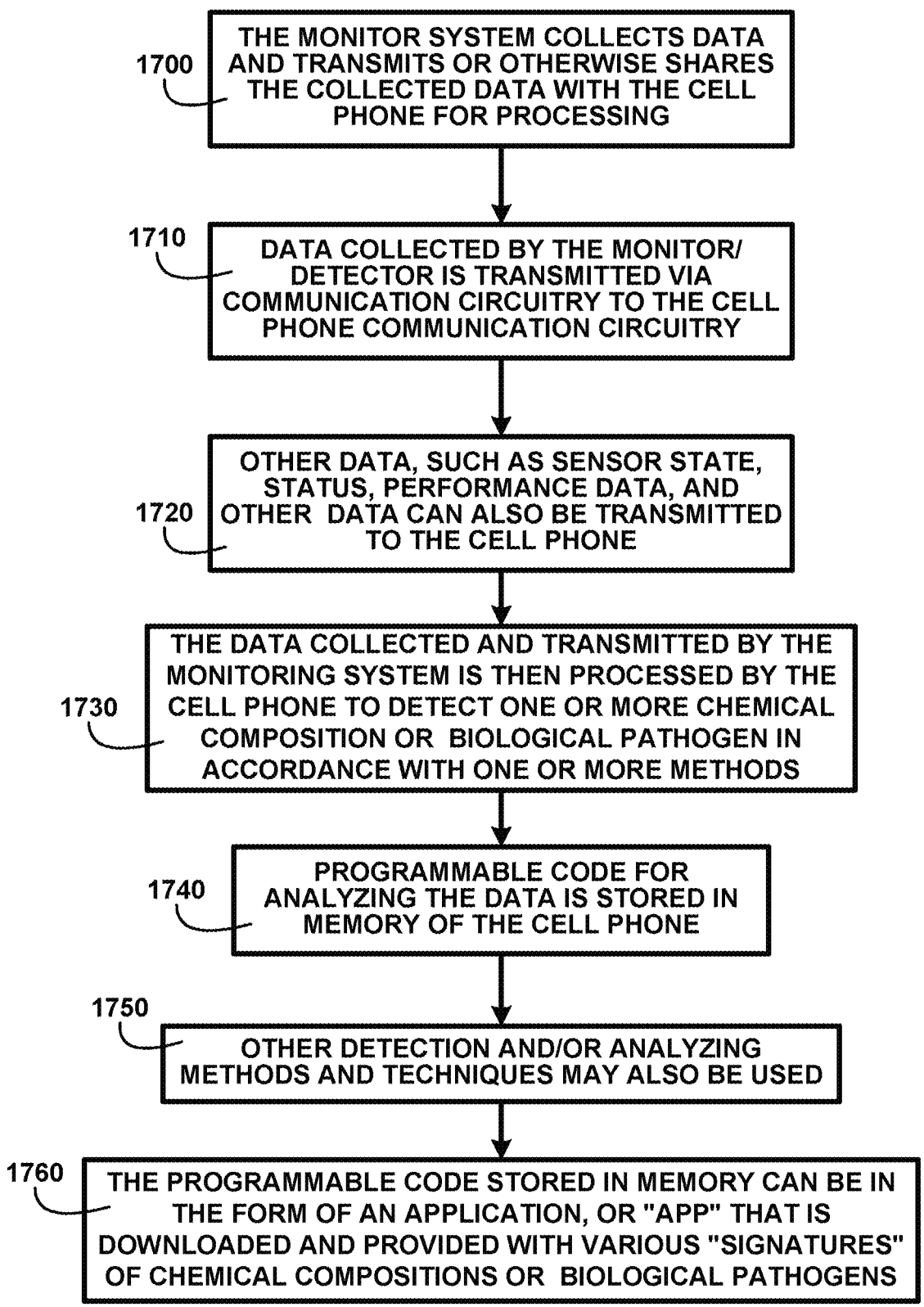
FIG. 17 shows a block diagram of an overview of a cell phone for processing of one embodiment.

A Cell Phone for Processing:

FIG. 17 shows a block diagram of an overview of a cell phone for processing of one embodiment. FIG. 17 shows the monitor system collects data and transmits or otherwise shares the collected data with the cell phone for processing 1700. The data collected by the monitor/detector is transmitted via communication circuitry to the cell phone communication circuitry 1710. Other data, such as sensor state, status, performance data, and other data can also be transmitted to the cell phone 1720. The data collected and transmitted by the monitoring system is then processed by the cell phone to detect one or more chemical composition or biological pathogen in accordance with one or more methods 1730.

Programmable code for analyzing the data is stored in memory of the cell phone 1740. Other detection and/or analyzing methods and techniques may also be used 1750 The programmable code stored in memory can be in the form of an application, or "app" that is downloaded and provided with various "signatures" of chemical compositions or biological pathogens 1760 of one embodiment.

Figure 18:
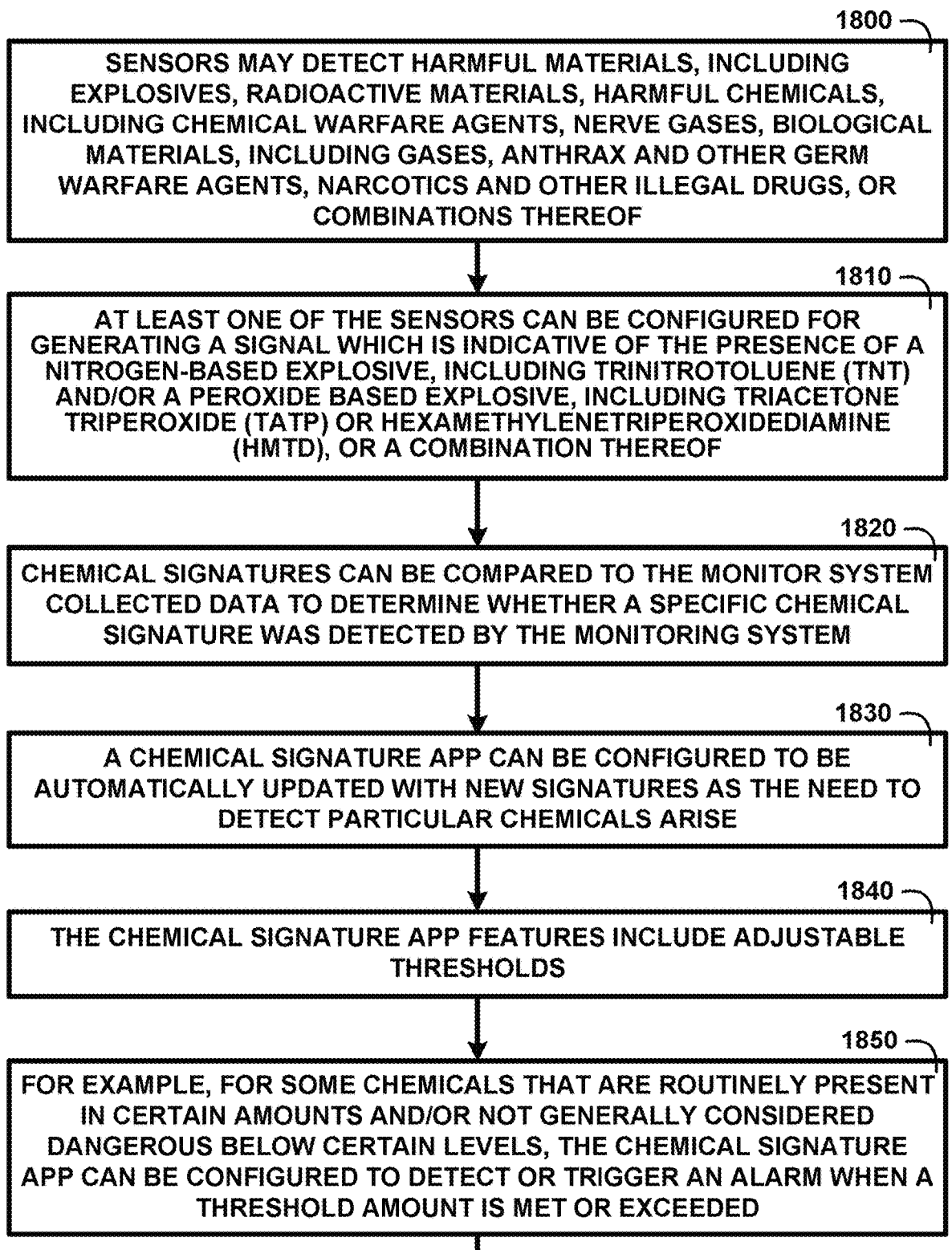
FIG. 18 shows a block diagram of an overview of sensors may detect harmful materials of one embodiment.

Sensors May Detect Harmful Materials:

FIG. 18 shows a block diagram of an overview of sensors may detect harmful materials of one embodiment. FIG. 18 shows sensors may detect harmful materials, including explosives, radioactive materials, harmful chemicals, including chemical warfare agents, nerve gases, biological materials, including gases, anthrax and other germ warfare agents, narcotics and other illegal drugs, or combinations thereof 1800. At least one of the sensors can be configured for generating a signal which is indicative of the presence of a nitrogen-based explosive, including trinitrotoluene (TNT) and/or a peroxide based explosive, including triacetone triperoxide (TATP) or hexamethylenetriperoxidediamine (HMTD), or a combination thereof 1810.

Chemical signatures can be compared to the monitor system collected data to determine whether a specific chemical signature was detected by the monitoring system 1820. A chemical signature app can be configured to be automatically updated with new signatures as the need to detect particular chemicals arise 1830. The chemical signature app features include adjustable thresholds 1840, for example, for some chemicals that are routinely present in certain amounts and/or not generally considered dangerous below certain levels, the chemical signature app can be configured to detect or trigger an alarm when a threshold amount is met or exceeded 1850. The description is continued in FIG. 19

Figure 19:
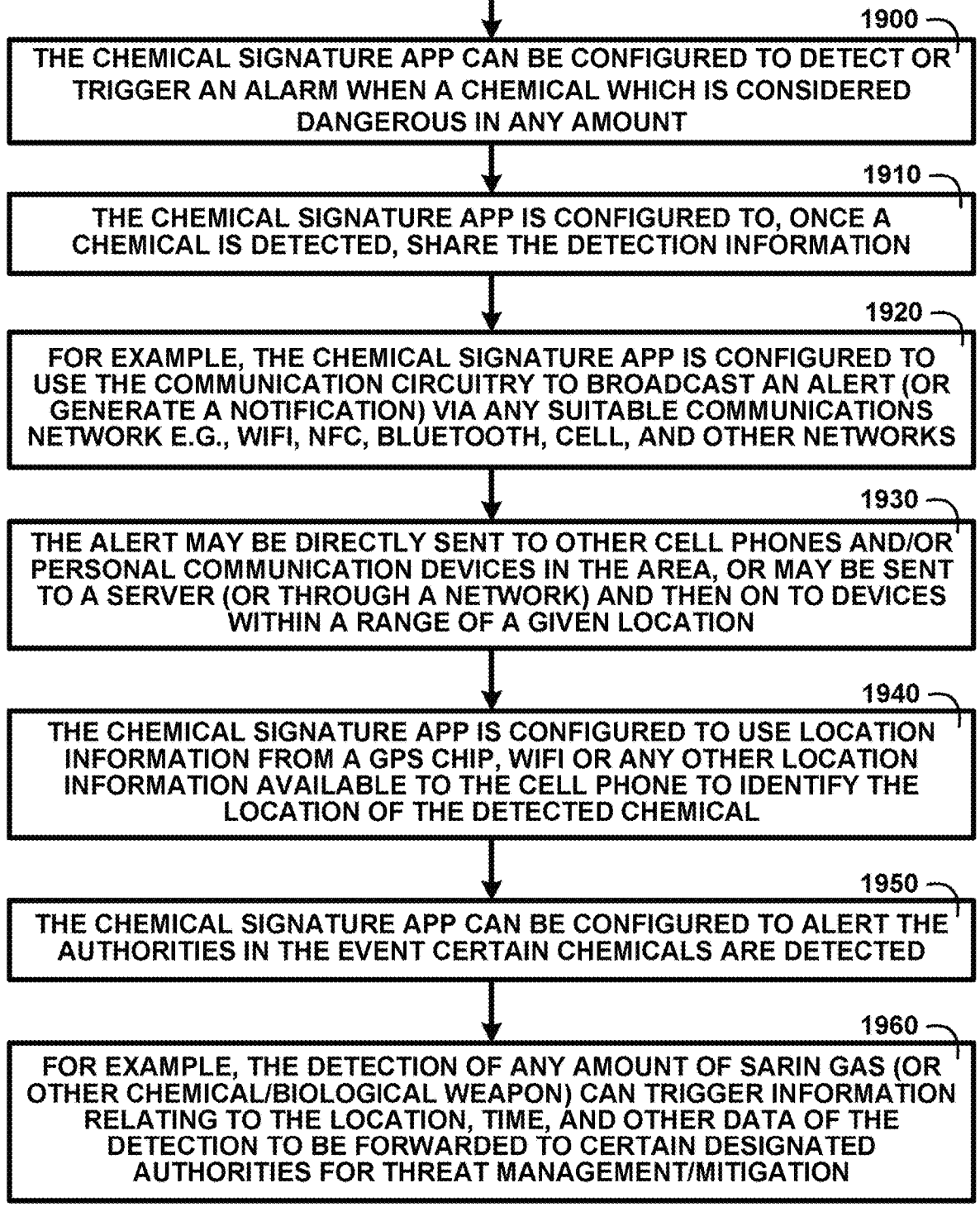
FIG. 19 shows a block diagram of an overview of a chemical signature app of one embodiment.

A Chemical Signature App:

FIG. 19 shows a block diagram of an overview of a chemical signature app of one embodiment. FIG. 19 shows a continuation from FIG. 18 shows the chemical signature app can be configured to detect or trigger an alarm when a chemical which is considered dangerous in any amount 1900. The chemical signature app is configured to, once a chemical is detected, share the detection information 1910, for example, the chemical signature app is configured to use the communication circuitry to broadcast an alert (or generate a notification) via any suitable communications network e.g., WIFI, NFC, Bluetooth, cell, and other networks 1920. The alert may be directly sent to other cell phones and/or personal communication devices in the area, or may be sent to a server (or through a network) and then on to devices within a range of a given location 1930.

The chemical signature app is configured to use location information from a GPS chip, WIFI or any other location information available to the cell phone to identify the location of the detected chemical 1940. The chemical signature app can be configured to alert the authorities in the event certain chemicals are detected 1950, for example, the detection of any amount of sarin gas (or other chemical/biological weapon) can trigger information relating to the location, time, and other data of the detection to be forwarded to certain designated authorities for threat management/mitigation 1960 of one embodiment.

Figure 20:
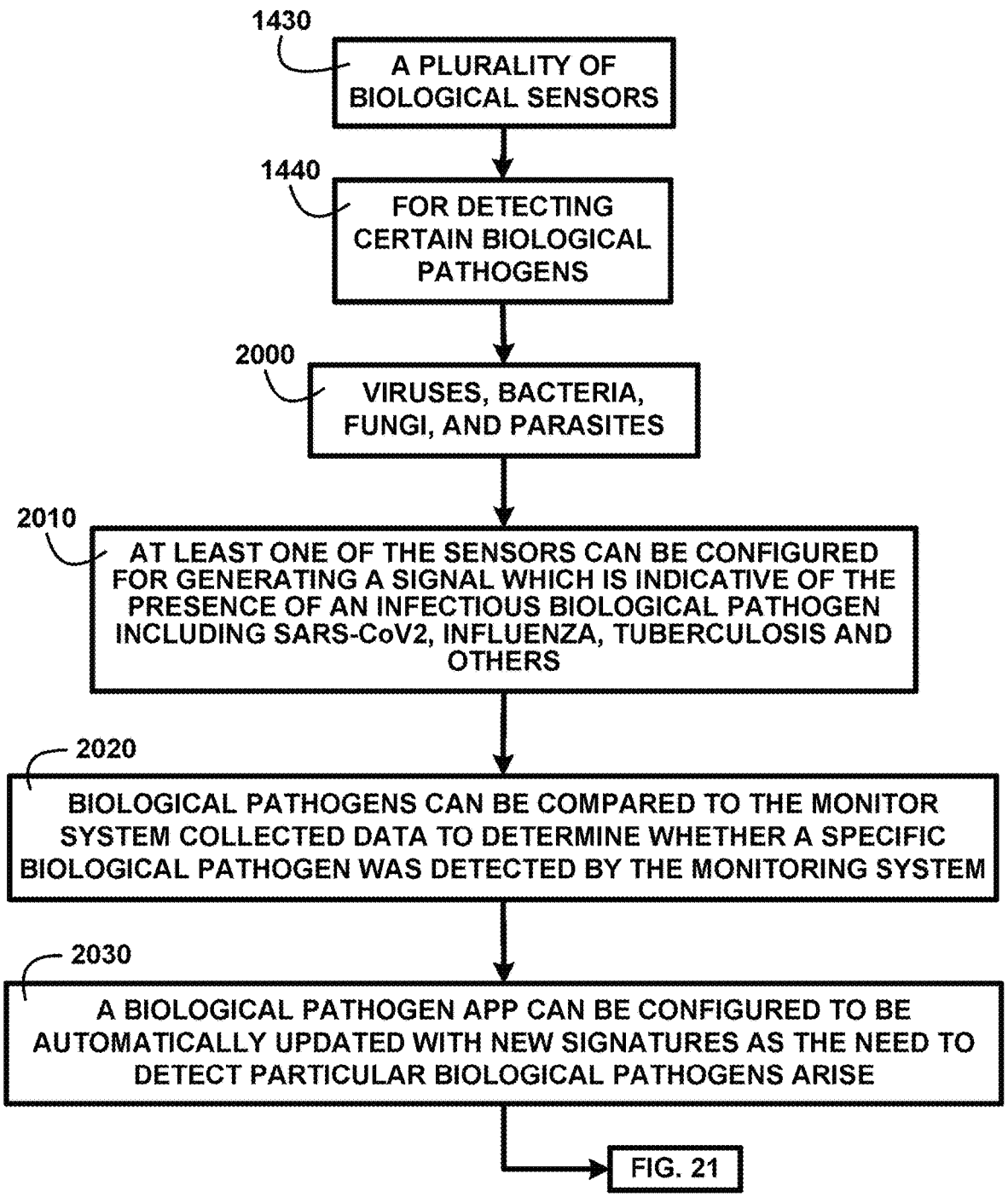
FIG. 20 shows a block diagram of an overview of a biological pathogen app of one embodiment.

A Biological Pathogen App:

FIG. 20 shows a block diagram of an overview of a biological pathogen app of one embodiment. FIG. 20 shows a plurality of biological sensors 1430 for detecting certain biological pathogens 1440 including viruses, bacteria, fungi, and parasites 2000. At least one of the sensors can be configured for generating a signal which is indicative of the presence of an infectious biological pathogen including SARS-CoV2, influenza, tuberculosis and others 2010. Biological pathogens can be compared to the monitor system collected data to determine whether a specific biological pathogen was detected by the monitoring system 2020. A biological pathogen app can be configured to be automatically updated with new signatures as the need to detect particular biological pathogens arise 2030. The description is continued in FIG. 21.

Communication Circuitry to Broadcast an Alert:

FIG. 21 shows a block diagram of an overview of communication circuitry to broadcast an alert of one embodiment. FIG. 21 shows a continuation from FIG. 20 the biological pathogen app can be configured to detect or trigger an alarm when a pathogen which is considered highly infectious is detected 2100. The biological pathogen app is configured to, once a highly infectious pathogen is detected, share the detection information 2110, for example, the biological pathogen app is configured to use the communication circuitry to broadcast an alert (or generate a notification) via any suitable communications network e.g., WIFI, NFC, Bluetooth, cell, and other networks 2120. The alert may be directly sent to other cell phones and/or personal communication devices in the area, or may be sent to a server (or through a network) and then on to devices within a range of a given location 2130 of one embodiment.

Figure 22:
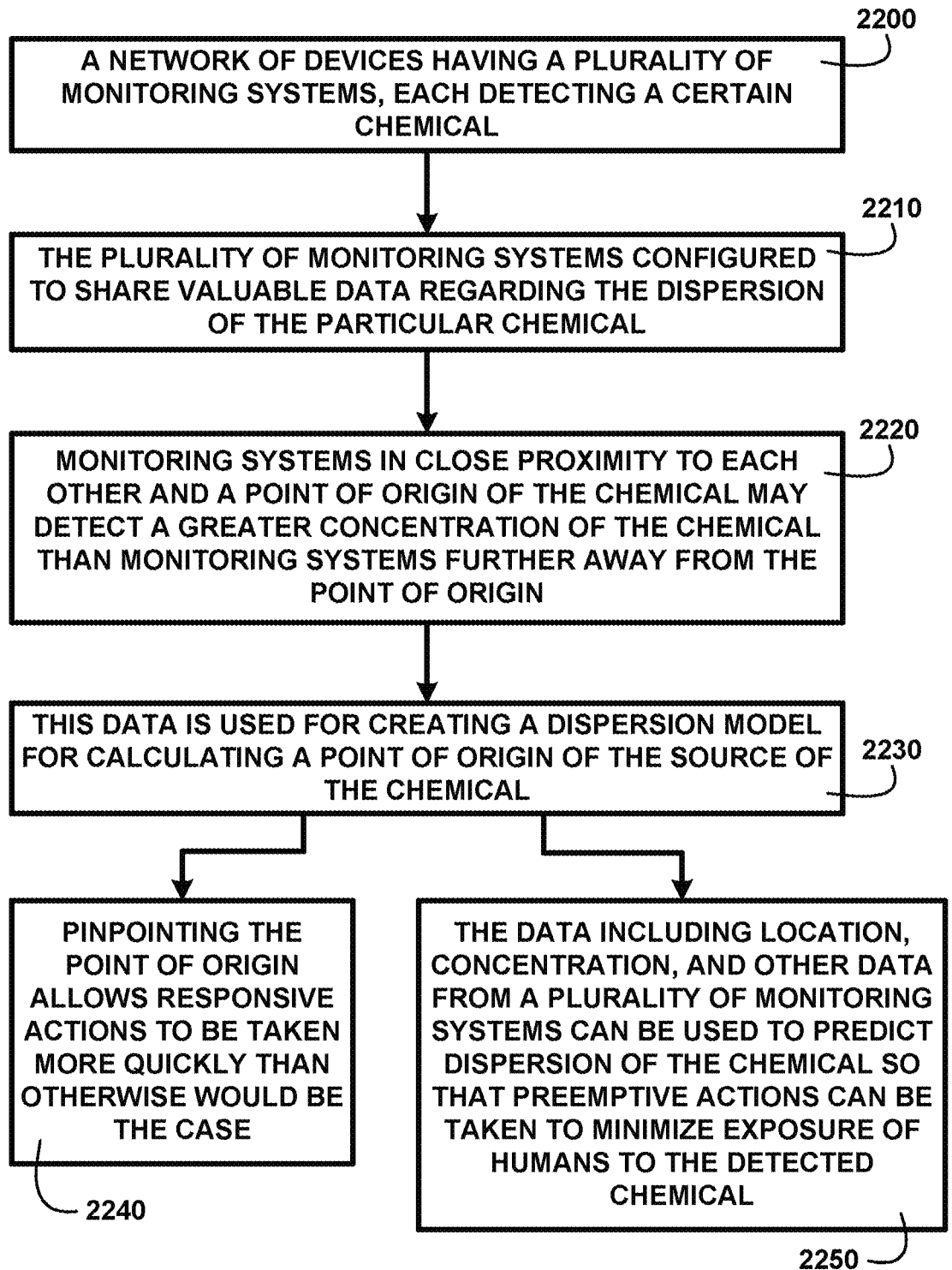
FIG. 22 shows a block diagram of an overview of a network of devices having a plurality of monitoring systems of one embodiment.

A Network of Devices Having a Plurality of Monitoring Systems:

FIG. 22 shows for illustrative purposes only an example of a network of devices having a plurality of monitoring systems of one embodiment. FIG. 22 shows a network of devices having a plurality of monitoring systems, each detecting a certain chemical 2200. The plurality of monitoring systems configured to share valuable data regarding the dispersion of the particular chemical 2210. Monitoring systems in close proximity to each other and a point of origin of the chemical may detect a greater concentration of the chemical than monitoring systems further away from the point of origin 2220. This data is used for creating a dispersion model for calculating a point of origin of the source of the chemical 2230. Pinpointing the point of origin allows responsive actions to be taken more quickly than otherwise would be the case 2240. The data including location, concentration, and other data from a plurality of monitoring systems can be used to predict dispersion of the chemical so that preemptive actions can be taken to minimize exposure of humans to the detected chemical 2250 of one embodiment.

Figure 23:
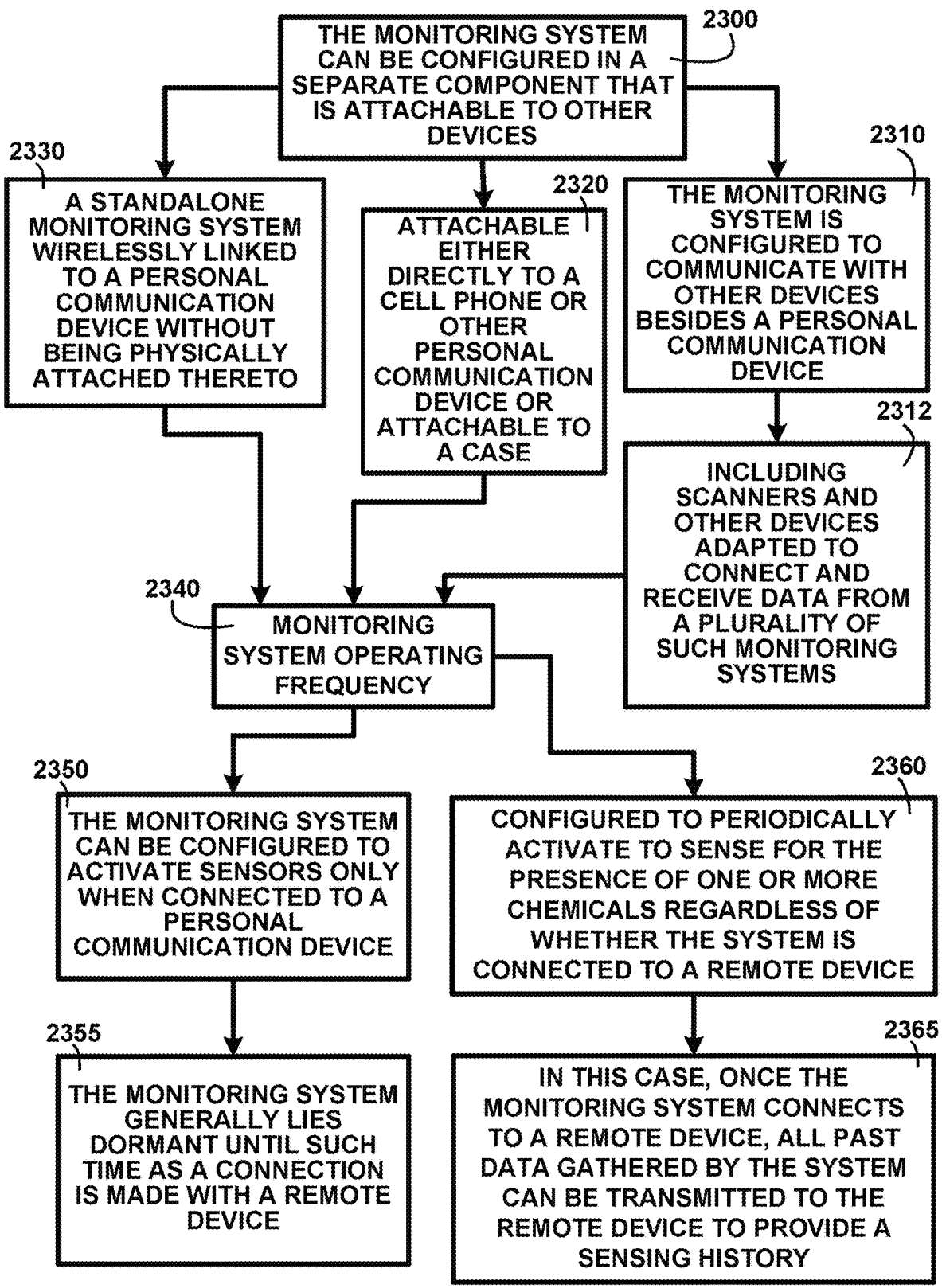
FIG. 23 shows a block diagram of an overview of the monitoring system configured in a separate component of one embodiment.

The Monitoring System Configured in a Separate Component:

FIG. 23 shows a block diagram of an overview of the monitoring system configured in a separate component of one embodiment. FIG. 23 shows the monitoring system can be configured in a separate component that is attachable to other devices 2300. The monitoring system is configured to communicate with other devices besides a personal communication device 2310 including scanners and other devices adapted to connect and receive data from a plurality of such monitoring systems 2312. The monitoring system is attachable either directly to a cell phone or other personal communication device or attachable to a case 2320. A standalone monitoring system wirelessly linked to a personal communication device without being physically attached thereto 2330 can be used. The monitoring system operating frequency 2340 can be varied for a particular use. The monitoring system can be configured to activate sensors only when connected to a personal communication device 2350. In this operating frequency the monitoring system generally lies dormant until such time as a connection is made with a remote device 2355. The monitoring system operating frequency 2340 can be configured to periodically activate to sense for the presence of one or more chemicals regardless of whether the system is connected to a remote device 2360. In this case, once the monitoring system connects to a remote device, all past data gathered by the system can be transmitted to the remote device to provide a sensing history 2365 of one embodiment.

Figure 24:
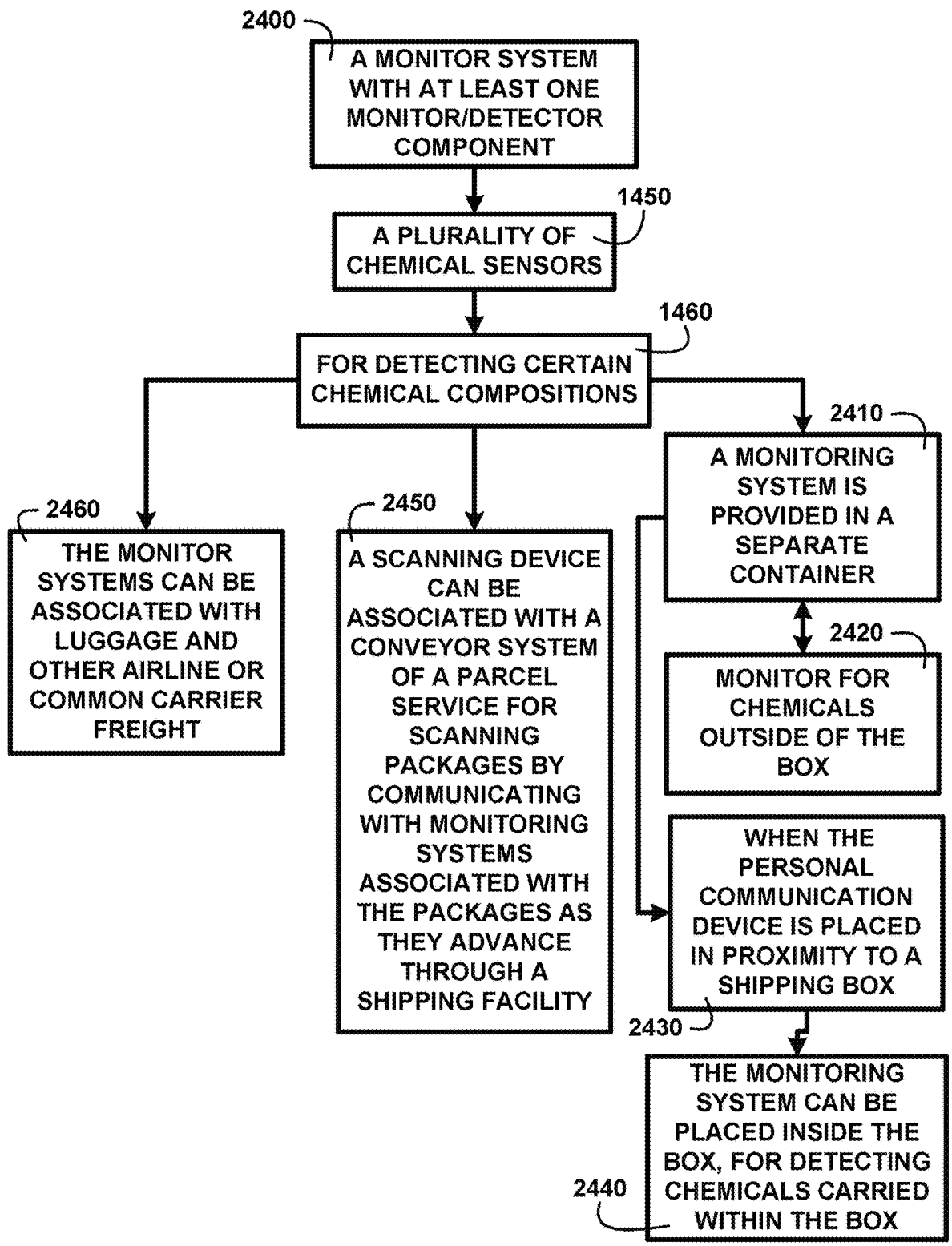
FIG. 24 shows a block diagram of an overview of a scanning device of one embodiment.

A Scanning Device:

FIG. 24 shows a block diagram of an overview of a scanning device of one embodiment. FIG. 24 shows a monitor system with at least one monitor/detector component 2400 and a plurality of chemical sensors 1450 for detecting certain chemical compositions 1460. A monitoring system is provided in a separate container 2410 to monitor for chemicals outside of the box 2420. When the personal communication device is placed in proximity to a shipping box 2430 the monitoring system transmits the data to the personal communication device. The monitoring system can be placed inside the box, for detecting chemicals carried within the box 2440. A scanning device can be associated with a conveyor system of a parcel service for scanning packages by communicating with monitoring systems associated with the packages as they advance through a shipping facility 2450. The monitor systems can be associated with luggage and other airline or common carrier freight 2460 of one embodiment.

Figure 25:
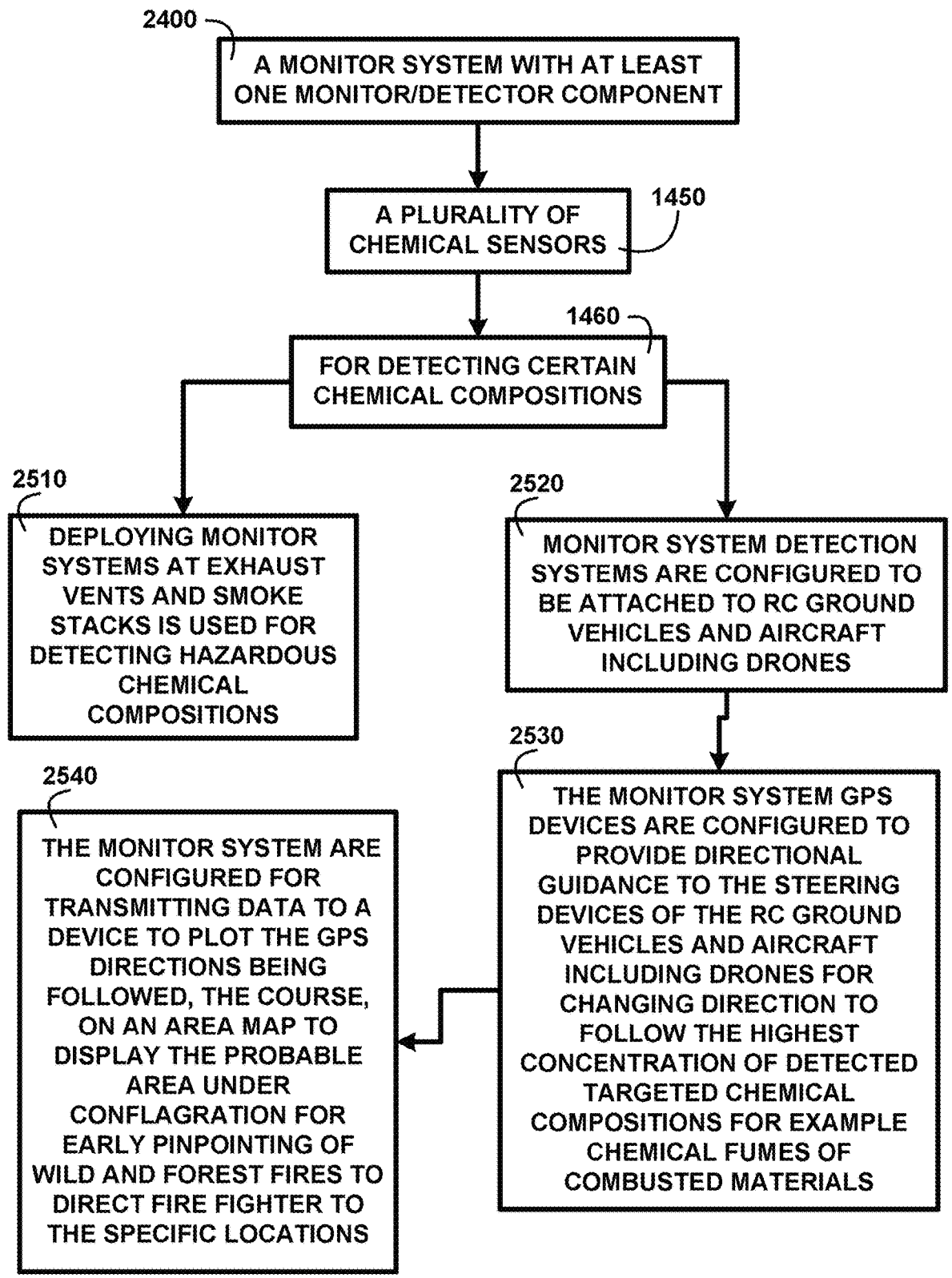
FIG. 25 shows a block diagram of an overview of RC ground vehicles and air craft of one embodiment.

RC Ground Vehicles and Aircraft:

FIG. 25 shows a block diagram of an overview of RC ground vehicles and air craft of one embodiment. FIG. 25 shows a monitor system with at least one monitor/detector component 2400 and a plurality of chemical sensors 1450 for detecting certain chemical compositions 1460. In one embodiment deploying monitor systems at exhaust vents and smoke stacks is used for detecting hazardous chemical compositions 2510. Monitor system detection systems are configured to be attached to RC ground vehicles and aircraft including drones 2520.

The monitor system GPS devices are configured to provide directional guidance to the steering devices of the RC ground vehicles and aircraft including drones for changing direction to follow the highest concentration of detected targeted chemical compositions for example chemical fumes of combusted materials 2530. The monitor system are configured for transmitting data to a device to plot the GPS directions being followed, the course, on an area map to display the probable area under conflagration for early pinpointing of wild and forest fires to direct fire fighter to the specific locations 2540 of one embodiment.

Figure 26:
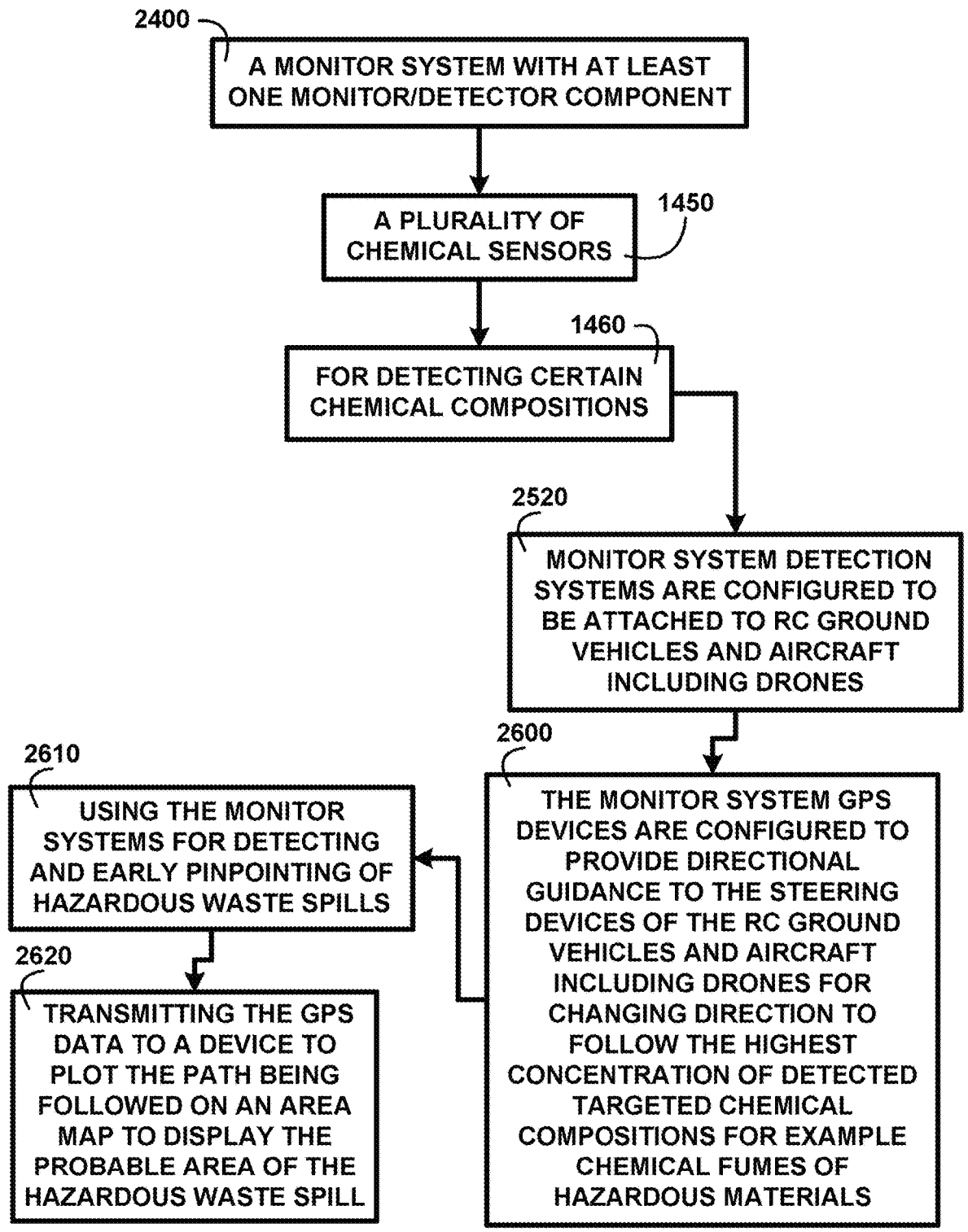
FIG. 26 shows a block diagram of an overview of directional guidance to the steering devices of one embodiment.

Directional Guidance to the Steering Devices:

FIG. 26 shows a block diagram of an overview of directional guidance to the steering devices of one embodiment. FIG. 26 shows a monitor system with at least one monitor/detector component 2400 with a plurality of chemical sensors 1450 for detecting certain chemical compositions 1460. Monitor system detection systems are configured to be attached to RC ground vehicles and aircraft including drones 2520. The monitor system GPS devices are configured to provide directional guidance to the steering devices of the RC ground vehicles and aircraft including drones for changing direction to follow the highest concentration of detected targeted chemical compositions for example chemical fumes of hazardous materials 2600. Using the monitor systems for detecting and early pinpointing of hazardous waste spills 2610. The monitor systems are configured for transmitting the GPS data to a device to plot the path being followed on an area map to display the probable area of the hazardous waste spill 2620 of one embodiment.

Figure 27:
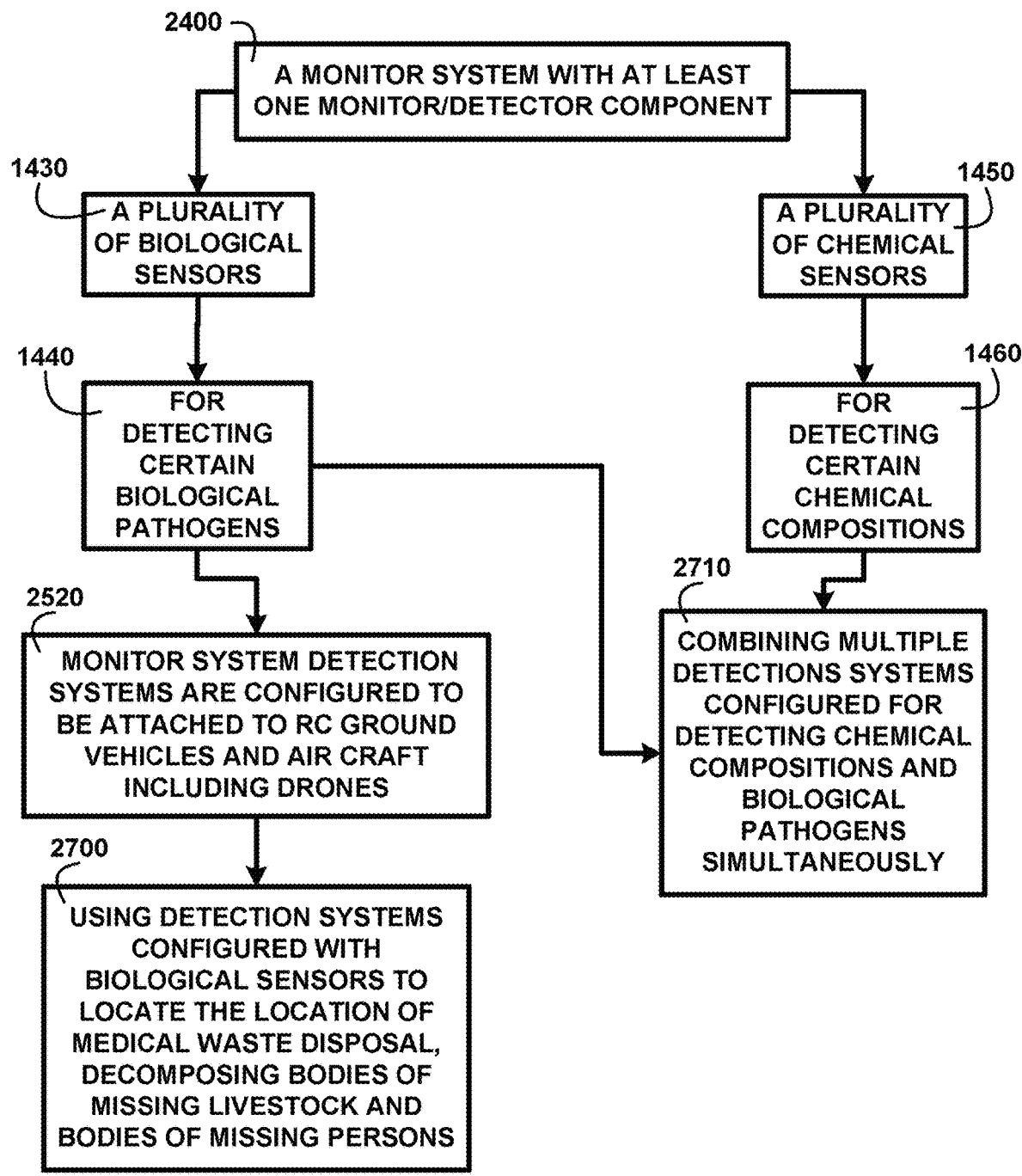
FIG. 27 shows a block diagram of an overview of location of medical waste disposal of one embodiment.

Location of Medical Waste Disposal:

FIG. 27 shows a block diagram of an overview of location of medical waste disposal of one embodiment. FIG. 27 shows a monitor system with at least one monitor/detector component 2400 with a plurality of chemical sensors 1450 for detecting certain chemical compositions 1460. In another embodiment the monitor system is configured with a plurality of biological sensors 1430 for detecting certain biological pathogens 1440. Some applications are configured for combining multiple detections systems configured for detecting chemical compositions and biological pathogens simultaneously 2710. The plurality of biological sensors 1430 for detecting certain biological pathogens 1440 can be used with the monitor system detection systems are configured to be attached to RC ground vehicles and aircraft including drones 2520. Application include using detection systems configured with biological sensors to locate the location of medical waste disposal, decomposing bodies of missing livestock and bodies of missing persons 2700 of one embodiment.

Figure 28:
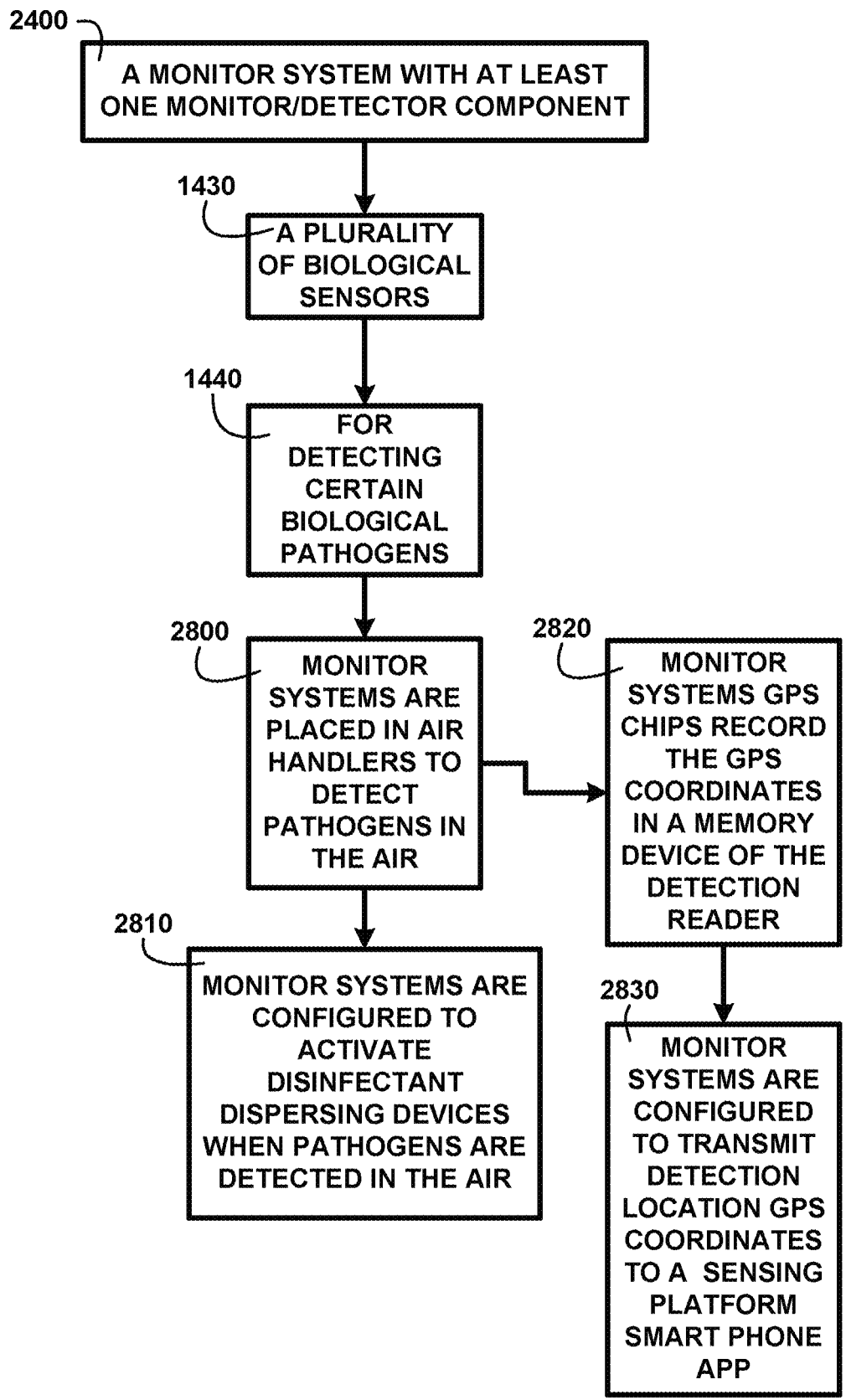
FIG. 28 shows a block diagram of an overview of monitor systems are placed in air handlers of one embodiment.

Monitor Systems are Placed in Air Handlers:

FIG. 28 shows a block diagram of an overview of monitor systems are placed in air handlers of one embodiment. FIG. 28 shows a monitor system with at least one monitor/detector component 2400 with a plurality of biological sensors 1430 for detecting certain biological pathogens 1440. Monitor systems are placed in air handlers to detect pathogens in the air 2800. Monitor systems are configured to activate disinfectant dispersing devices when pathogens are detected in the air 2810. Monitor systems GPS chips record the GPS coordinates in a memory device of the detection reader 2820. The monitor systems are configured to transmit detection location GPS coordinates to a sensing platform smart phone app 2830 of one embodiment.

The foregoing has described the principles, embodiments and modes of operation of the present invention. However, the invention should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

What is claimed is:

1. A method, comprising:
    providing an air monitoring system having a plurality of impedimetric sensors for detecting predetermined pathogens;
    providing circuit power and impedance measurement circuitry to operate the impedimetric sensors;
    integrating the air monitoring system into air handlers to detect the predetermined pathogens of human saliva droplets in air flow passing through the air handlers that are in contact with the plurality of sensors;
    providing disinfectant within the air handlers with dispersing devices that are activated when the predetermined pathogens of the human saliva droplets are detected in the air flow;
    providing a detection reader with a location tracking module coupled to the air monitoring system to track coordinates of the detected predetermined pathogen;
    wherein the detection reader is coupled to the air monitoring system via the location tracking module for analyzing and identifying the predetermined detected pathogen; and
    providing at least one communication device coupled to the detection reader for accessing the location coordinates of the detection reader and the detected predetermined pathogen.

2. The method of claim 1, further comprising providing a memory device coupled to the detection reader for recording GPS location coordinates of the location tracking module.

3. The method of claim 1, further comprising providing an active air flow induction device that may include at least one from a group of concentrators, vacuums and magnetic coupled to the air monitoring system for inducing a continuous flow of air across the plurality of sensors from a group consisting of at least one of biological sensors, electrochemical sensors, Micro Electro-Mechanical System (MEMs) sensors, or chemical and gas sensors.

4. The method of claim 1, further comprising providing a smart phone as the at least one communication device.

5. The method of claim 1, wherein analyzing and identifying the predetermined detected pathogens is performed with a sensing app operating on the smart phone app.

6. The method of claim 1, further comprising providing a disinfectant within the air handlers with dispersing devices that kills 99.9% of the predetermined pathogens.

7. An apparatus, comprising:
    an air monitoring system having a plurality of biological sensors configured to detect predetermined biological pathogens;
    wherein the air monitoring system is integrated into air handlers and configured to detect the predetermined biological pathogens of human saliva droplets in air flow passing through the air handlers that are in contact with the plurality of biological sensors;
    a detection application operating on a mobile device that is coupled to the plurality of sensors, wherein the detection application is configured to transmit alerts and information to a user of the mobile device about the detected predetermined pathogens;
    disinfectant dispersing devices coupled to the air monitoring system and the detection application and configured to disperse disinfectant within the air handlers as directed and controlled by the user via the detection application;
    a detection reader with a location module coupled to the mobile device that produces location coordinates, wherein the detection reader is coupled to the air monitoring system and configured to analyze and identify the predetermined detected biological pathogen of the human saliva droplets; and
    at least one communication device coupled to the detection reader and configured to access the location coordinates of the detection reader and the detected predetermined pathogen.

8. The apparatus of claim 7, further comprising a memory device coupled to the detection reader and configured for recording GPS location coordinates and providing the GPS location coordinates to designated users.

9. The apparatus of claim 7, further comprising an active air flow induction device coupled to the air monitoring system and configured for inducing a continuous flow of air across the plurality of biological sensors.

10. The apparatus of claim 7, wherein the mobile device is a smart phone.

11. The apparatus of claim 7, further comprising an active air flow induction device coupled to the air monitoring system for inducing a continuous flow of air in a fixed location with restricted air movement including locations where cargo and baggage are stored on aircraft.

12. The apparatus of claim 7, wherein the mobile device is a smart phone with an app wirelessly coupled to the detection reader and the detection application and configured for analyzing sensor detected biological pathogens and for displaying sensor detected analysis data on the user's digital device.

13. The apparatus of claim 7, further comprising a GPS chip coupled to the air monitoring system and configured for receiving GPS coordinates and recording the GPS coordinates in a memory device.

14. An apparatus, comprising:
an air monitoring system having a plurality of biological sensors and a detection sensor configured to detect predetermined biological pathogens, wherein at least one biological sensor is an impedimetric biosensor for detecting a SARS-CoV-2 virus and its variants of human saliva droplets;
wherein the air monitoring system is integrated into air handlers and configured to detect the predetermined biological pathogens in air flow passing through the air handlers that are in contact with the plurality of biological sensors;
an active air flow induction device coupled to the air monitoring system and configured for inducing a continuous flow of air across the plurality of biological sensors;
disinfectant dispersing devices configured to disperse disinfectant within the air handlers when the predetermined biological pathogens are detected in the air flow;
a detection reader coupled to the air monitoring system and having a location module that produces location coordinates, wherein the detection reader is configured to analyze and identify the predetermined detected biological pathogen; and
at least one smart phone coupled to the detection reader and configured to access the location coordinates of the detection reader and the detected predetermined pathogen of the human saliva droplets.

15. The apparatus of claim 14, further comprising, air flow directional devices with an independent power supply, fans and micro pumps, concentrators, vacuum, magnetic and active air flow inducing devices coupled to the active air flow induction device.

16. The apparatus of claim 14, wherein the active air flow induction device is configured to induce a continuous flow of air in a fixed location with restricted air movement including in a cargo and baggage storage compartment of an aircraft.

17. The apparatus of claim 14, wherein the smart phone is coupled to a remote server and coupled to plural remote smart phones.

18. The apparatus of claim 14, wherein the location coordinates of the detection reader and the detected predetermined pathogen are transmitted to a network for sharing with plural users.

19. The apparatus of claim 14, wherein the disinfectant dispersing devices are configured to be controlled by a user to allow manual dispersion of the disinfectant.

20. The apparatus of claim 14, further comprising at least one GPS coordinates location identification device coupled to the air monitor system configured for transmitting GPS coordinates to a memory device of the detection reader configured for recording the GPS coordinates and for wirelessly transmitting detection locations GPS coordinates to the biological pathogen app to plural remote users.

* * * * *